(12) United States Patent
Park et al.

(10) Patent No.: US 12,157,121 B2
(45) Date of Patent: Dec. 3, 2024

(54) HIGH-SPEED POLYMERASE CHAIN REACTION ANALYSIS PLATE

(71) Applicant: BIONEER CORPORATION, Daejeon (KR)

(72) Inventors: Han Oh Park, Daejeon (KR); Jong Kab Kim, Gyeongsangbuk-Do (KR); Yang Won Lee, Daejeon (KR); Sang Ryoung Park, Daejeon (KR)

(73) Assignee: Bioneer Corporation, Daejeon (KR)

( * ) Notice: Subject to any disclaimer, the term of this patent is extended or adjusted under 35 U.S.C. 154(b) by 198 days.

(21) Appl. No.: 17/040,389

(22) PCT Filed: Mar. 22, 2019

(86) PCT No.: PCT/KR2019/003376
§ 371 (c)(1),
(2) Date: Sep. 22, 2020

(87) PCT Pub. No.: WO2019/182407
PCT Pub. Date: Sep. 26, 2019

(65) Prior Publication Data
US 2021/0053059 A1    Feb. 25, 2021

(30) Foreign Application Priority Data

Mar. 23, 2018  (KR) ......................... 10-2018-0033934

(51) Int. Cl.
*B01L 3/00*   (2006.01)
*C12Q 1/6806* (2018.01)
(Continued)

(52) U.S. Cl.
CPC ...... *B01L 3/502738* (2013.01); *C12Q 1/6806* (2013.01); *C12Q 1/686* (2013.01);
(Continued)

(58) Field of Classification Search
CPC ......... B01L 3/502738; B01L 2200/027; C12Q 1/6806; C12Q 1/6874
See application file for complete search history.

(56) References Cited

U.S. PATENT DOCUMENTS

| 7,338,637 B2 | 3/2008 | Pease et al. |
| 8,222,023 B2 * | 7/2012 | Battrell ................. B01L 3/5027 435/288.5 |

(Continued)

FOREIGN PATENT DOCUMENTS

| CN | 1767898 A | 3/2006 |
| CN | 101418868 A | 4/2009 |

(Continued)

OTHER PUBLICATIONS

Charles Molnar and Jane Gair, "Concepts of Biology", 2015, B.C. Open Collection, 1st Canadian Edition, p. 320 (Year: 2015).*

(Continued)

*Primary Examiner* — Rebecca M Fritchman
*Assistant Examiner* — Mickey Huang
(74) *Attorney, Agent, or Firm* — AJU IP Global PLLC

(57) ABSTRACT

The present invention relates to the structure of an analysis plate applied to a high-speed polymerase chain reaction (PCR), and to a PCR analysis plate used for implementing an analysis of a real-time PCR, a real-time nested PCR and a post-PCR lateral flow hybridization reaction. The present invention is provided with: a check valve for enabling the maintaining of positive pressure when an elastic film expands into a convex form by having a solution pushed therein by the positive pressure; a lateral flow analysis module for analyzing a post-PCR follow-up PCR or lateral flow; and a shut-off valve enabling the controlling of the movement of the solution after each reaction ends. A high-speed PCR analysis plate may be provided whereby, by pressing, by means of a temperature-controllable heating (Continued)

block, the elastic film, which is in a convex form by the solution, of a PCR unit, a PCR solution may undergo rapid temperature circulation with minimum heat resistance, and a PCR dried material and a nucleic acid solution may be homogenized and mixed.

15 Claims, 13 Drawing Sheets

(51) Int. Cl.
   *C12Q 1/686* (2018.01)
   *C12Q 1/6874* (2018.01)
(52) U.S. Cl.
   CPC ...... *C12Q 1/6874* (2013.01); *B01L 2200/027* (2013.01); *B01L 2300/049* (2013.01); *B01L 2300/0819* (2013.01); *B01L 2300/0864* (2013.01); *B01L 2300/087* (2013.01); *B01L 2300/123* (2013.01); *B01L 2300/1827* (2013.01); *B01L 2400/0478* (2013.01); *B01L 2400/0605* (2013.01)

(56) References Cited

U.S. PATENT DOCUMENTS

| | | |
|---|---|---|
| 8,382,454 B2 | 2/2013 | Aso |
| 9,063,121 B2 | 6/2015 | Bru Gilbert et al. |
| 9,309,879 B2 | 4/2016 | Schmidt et al. |
| 9,757,724 B2 | 9/2017 | Rothacher et al. |
| 10,100,949 B2 | 10/2018 | Takano |
| 2003/0148535 A1 | 8/2003 | Colin |
| 2004/0110167 A1 | 6/2004 | Gerdes et al. |
| 2009/0023201 A1 | 1/2009 | Hongo et al. |
| 2011/0014606 A1 | 1/2011 | Steinmetzer et al. |
| 2012/0276582 A1* | 11/2012 | Ritzen ............... B01L 3/502715 435/39 |
| 2012/0276592 A1 | 11/2012 | Daub et al. |
| 2013/0230860 A1* | 9/2013 | Park ...................... B01L 3/0227 435/6.12 |
| 2013/0230906 A1* | 9/2013 | Martinelli ................ G01N 1/28 435/283.1 |
| 2013/0267016 A1 | 10/2013 | Niemz et al. |
| 2013/0294981 A1 | 11/2013 | Takahashi et al. |
| 2014/0328733 A1* | 11/2014 | Prakash ............ B01L 3/502715 422/537 |
| 2015/0290639 A1 | 10/2015 | Evtodienko |
| 2016/0193603 A1 | 7/2016 | Battrell et al. |
| 2017/0234866 A1* | 8/2017 | Hamad-Schifferli ....................... G01N 33/54306 506/9 |
| 2019/0119727 A1 | 4/2019 | Miyamoto et al. |

FOREIGN PATENT DOCUMENTS

| | | | |
|---|---|---|---|
| CN | 103402640 A | | 11/2013 |
| CN | 107339228 A | | 10/2017 |
| CN | 107532737 A | | 1/2018 |
| CN | 218561421 U | * | 3/2023 |
| EP | 3290760 A1 | | 3/2018 |
| IN | 104582849 A | | 4/2015 |
| JP | 2006-234590 A | | 9/2006 |
| JP | 2008-263959 A | | 6/2008 |
| JP | 2008-228735 A | | 10/2008 |
| JP | 2010-508039 A | | 3/2010 |
| JP | 2011-203181 A | | 10/2011 |
| KR | 10-20100020394 A | * | 8/2008 |
| KR | 101420568 B1 | | 7/2014 |
| KR | 101724281 B1 | | 4/2017 |
| KR | 101768040 B1 | | 8/2017 |
| WO | WO-2016148646 A1 | | 9/2016 |
| WO | 2018003550 A1 | | 1/2018 |

OTHER PUBLICATIONS

Ahn Yoo Min, Ha Seung Mo, Lee Dong Ho, Kim Hyun Joong, Hwang Seung-Yong, KR-10-20100020394A translation, 2008, KIPO (Year: 2008).*

Muhammad Sajid, Abdel-Nasser Kawde, Muhammad Daud, "Designs, formats and applications of lateral flow assay: A literature review", Sep. 16, 2014, Journal of Saudi Chemical Society, vol. 19, p. 689-705 (Year: 2014).*

Chia-Hsiang Chen, "Development of a Melting Curve-Based Allele-Specific PCR of Apolipoprotein E (APOE) Genotyping Method for Genomic DNA, Guthrie Blood Spot, and Whole Blood", Apr. 2016, ResearchGate (Year: 2016).*

Yan et al., CN-218561421-U translation, 2023, USPTO (Year: 2023).*

Extended European Search Report for corresponding European Application Serial No. 19772460.2 issued Jun. 10, 2021.

Partial Search Report for corresponding European Patent Application No. 19772460.2, issued Jan. 27, 2021.

International Search Report and Written Opinion of the International Searching Authority, issued in PCT/KR2019/003376, mailed Jul. 11, 2019; ISA/KR.

Christian D. Ahrberg, et al "Polymaerase chain reaction in microfluidic devices", Lab Chip, 16, (2016).

Martin U. Kopp et al "Chemical Amplification: Continuous-Flow PCR on a Chip", Science, vol. 280, (May 15, 1998).

Xun Mao, et al "Disposable Nucleic Acid Biosensors Based on Gold Nanoparticle Probes and Lateral Flow Strip", Analytical Chemistry, vol. 81, No. 4 (Feb. 15, 2009).

Hideo Nakano, et al "High Speed Polymerase Chain Reaction in Constant Flow", Bioscience, Biotechnology, and Biochemistry, 58:2, pp. 349-352 (Jun. 12, 2014).

Peter Wilding, et al "PCR in a Silicon Microstructure" Clin. Chem. 40/9, pp. 1815-1818 (1994).

Christine I. Wooddell, et al "Use of Asymmetric PCR to Generate Long Primers and Single-stranded DNA for Incorporating Cross-linking Analogs into Specific Sites in a DNA Probe", Cold Spring Harbor Laboratory Press, Genome Res. pp. 886-892 (1996).

Office Action for corresponding Chinese patent application No. 201980028664.X, dated Sep. 1, 2021, nine pages.

Office Action for corresponding Japanese patent application No. 2020-551283, dated Nov. 2, 2021, six pages.

Office Action for corresponding Japanese Patent Application No. 2020-551283 issued Aug. 5, 2022, with English machine translation.

* cited by examiner

[Fig.1]
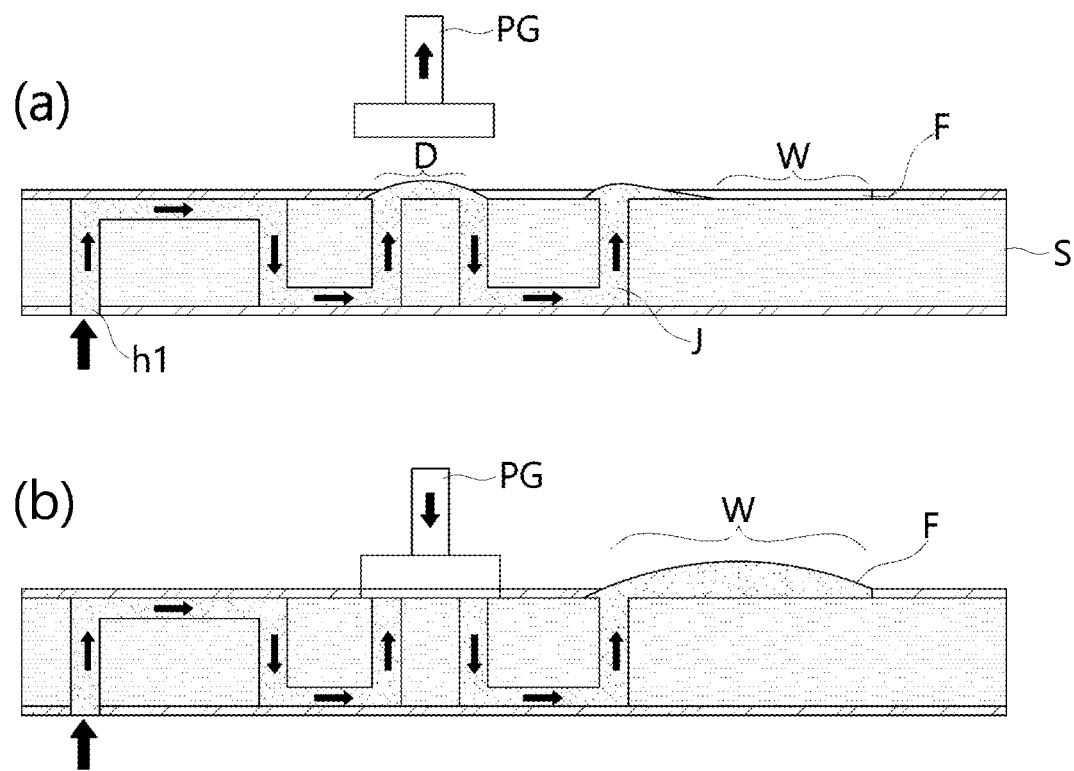

[Fig.2]
(a)
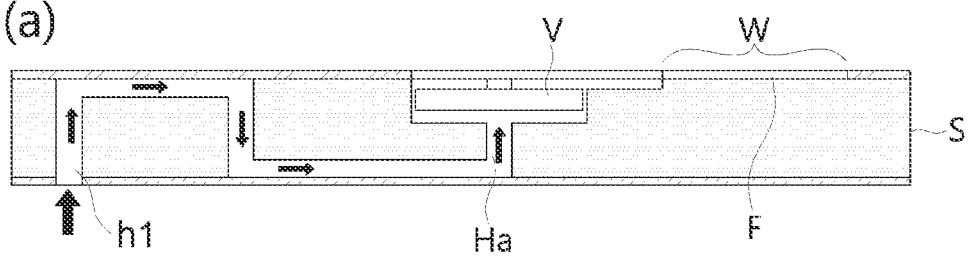
(b)
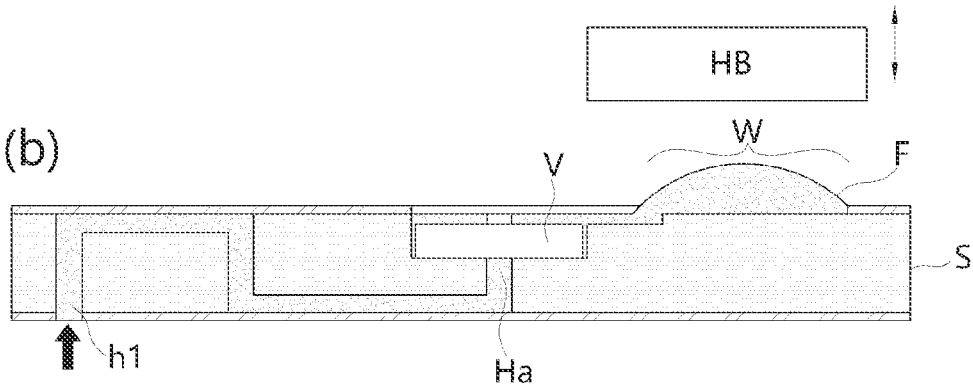

[Fig.3]
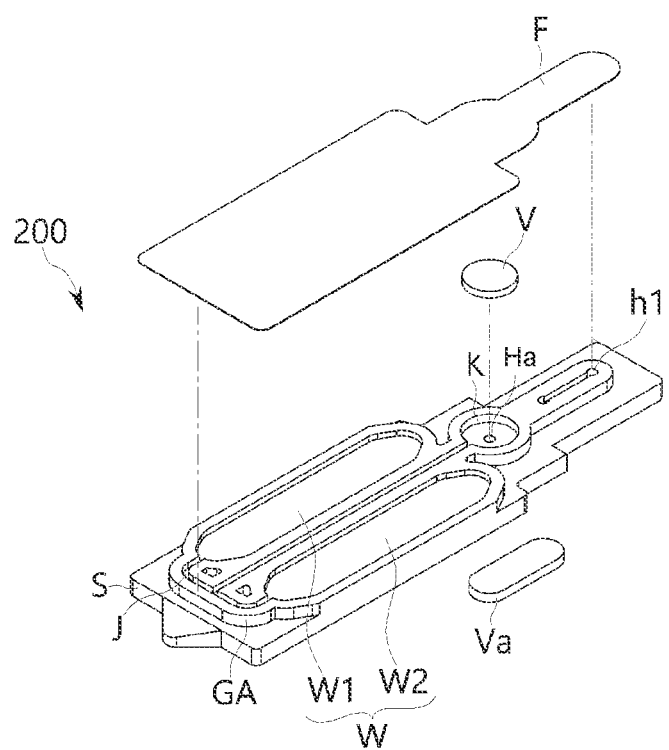

[Fig.4]
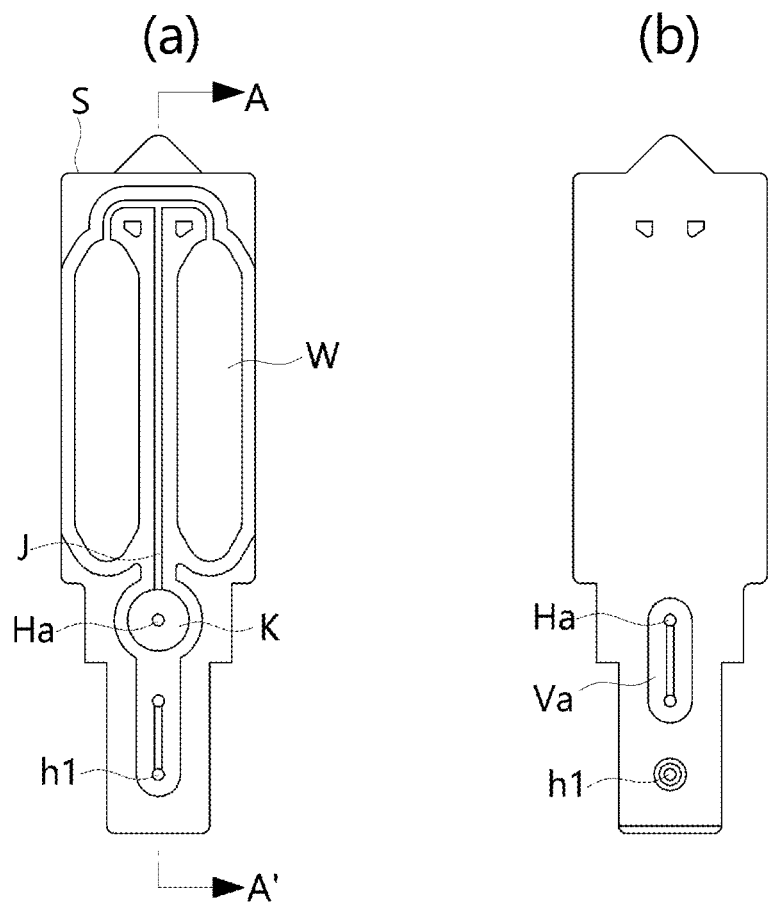
[Fig.5]
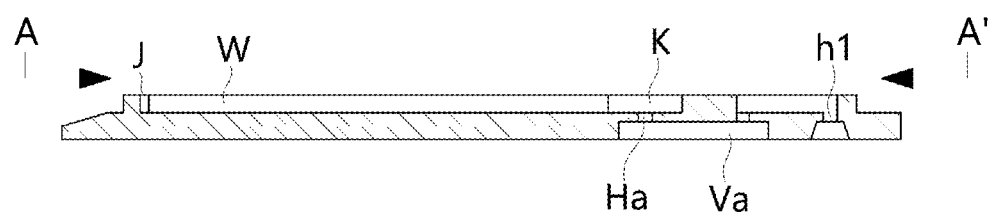

[Fig.6]
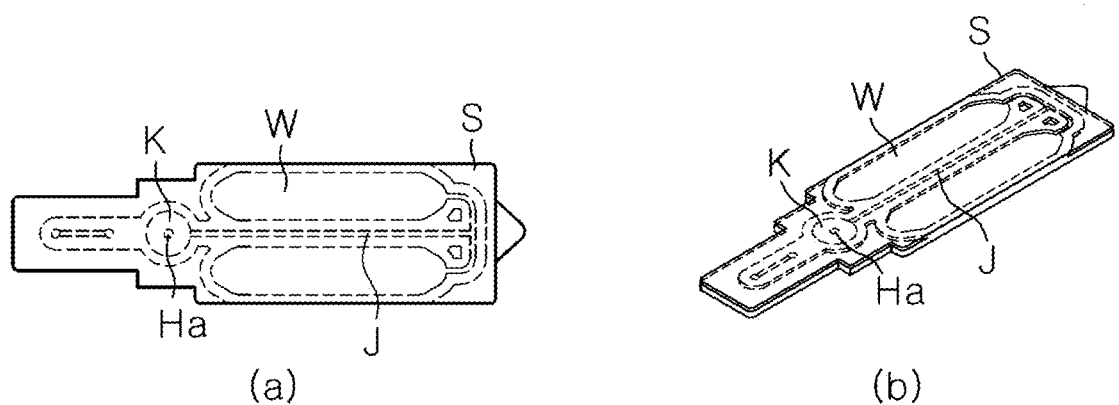
(a)                (b)
[Fig.7]
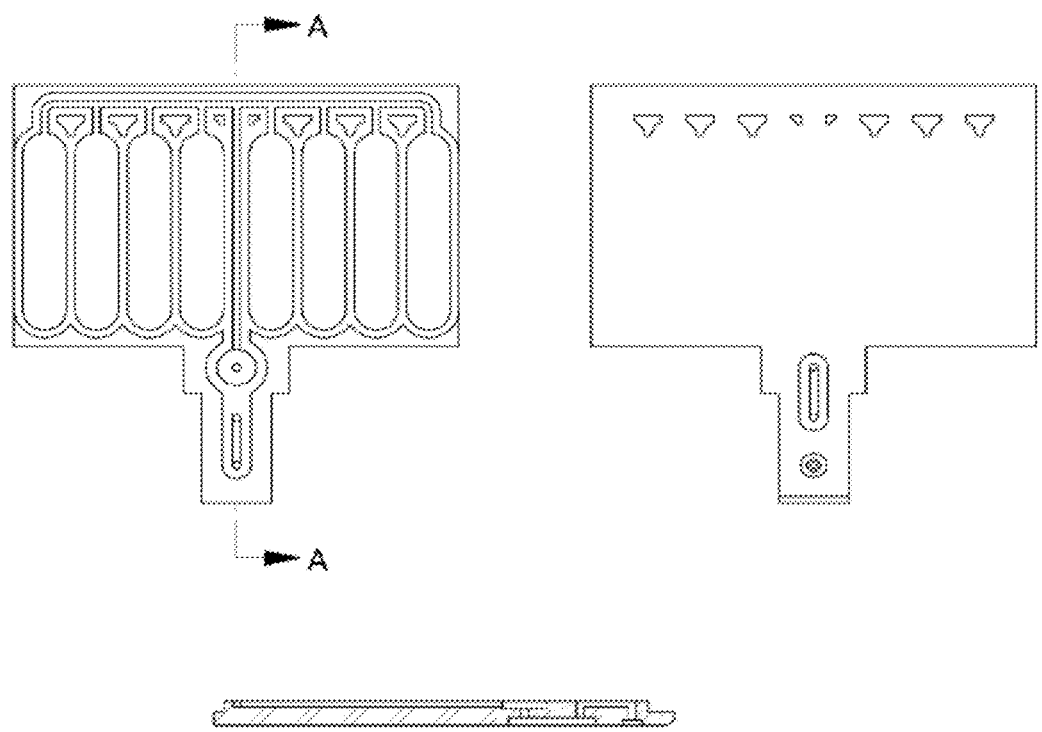

[Fig.8]
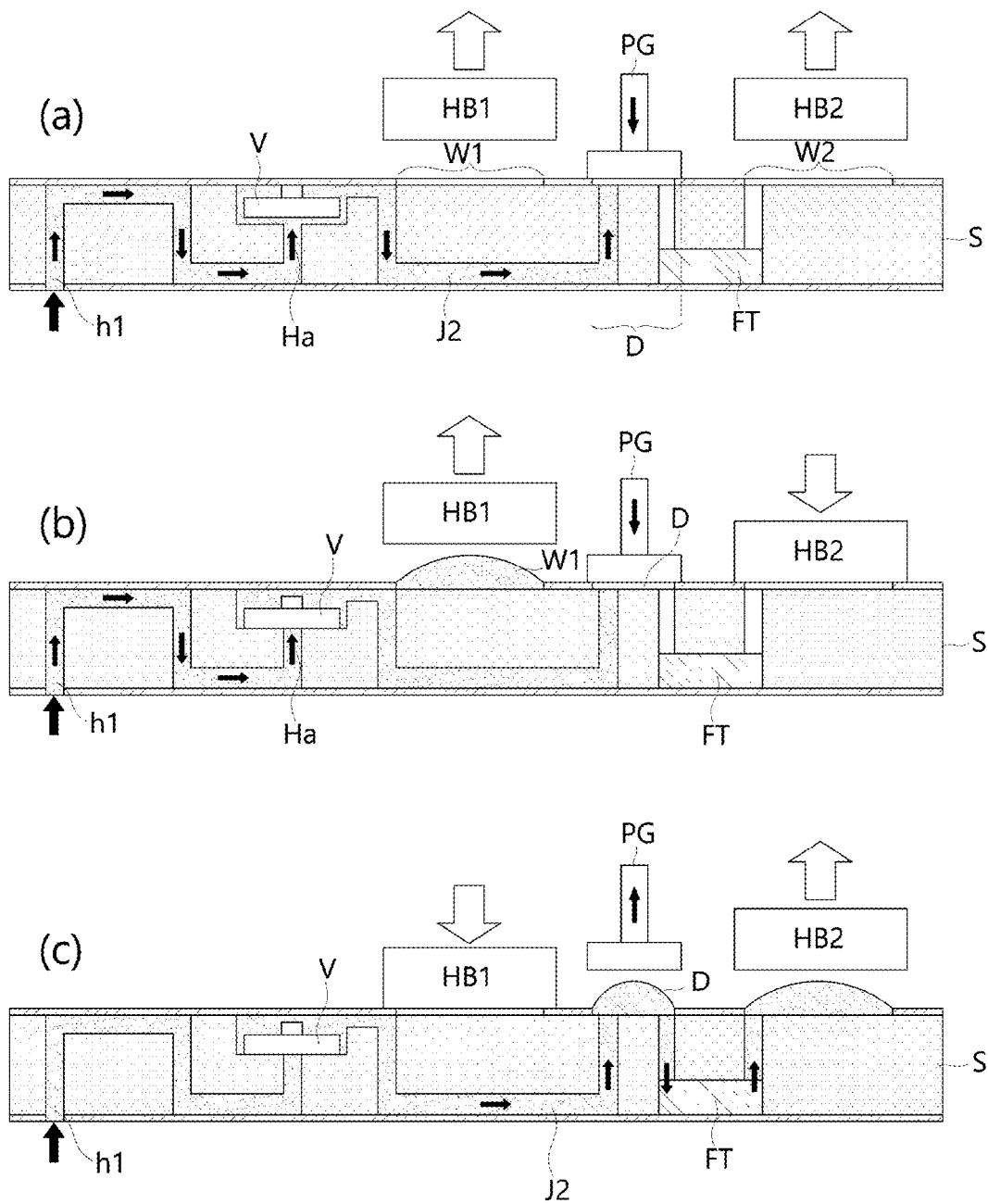

[Fig.9]
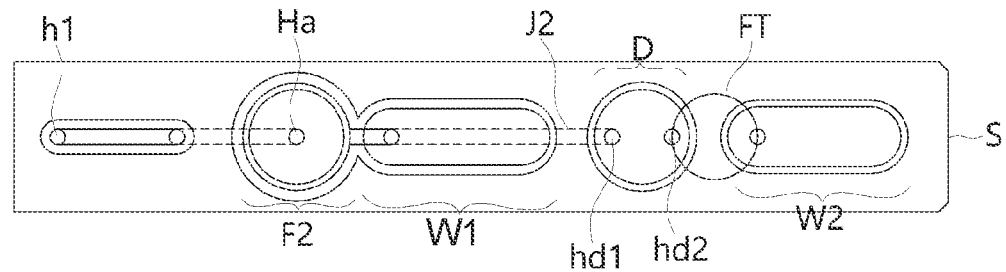
[Fig.10]
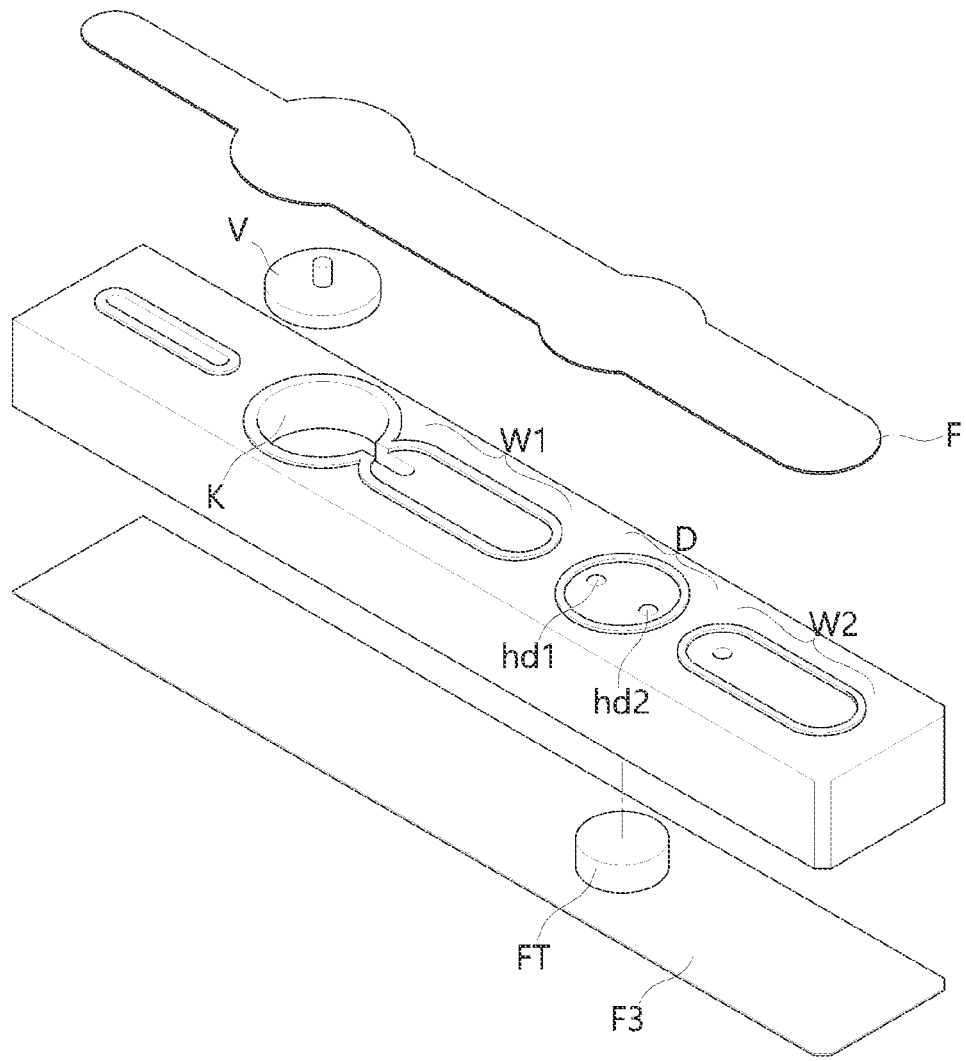

[Fig.11]
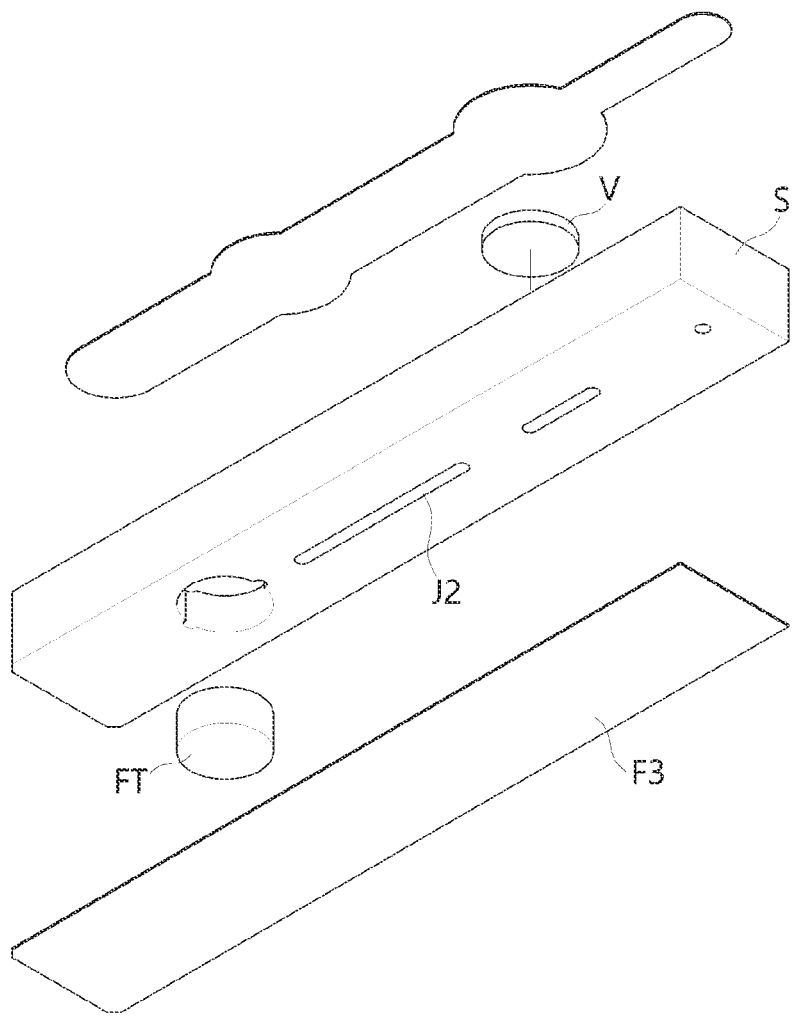

[Fig.12]
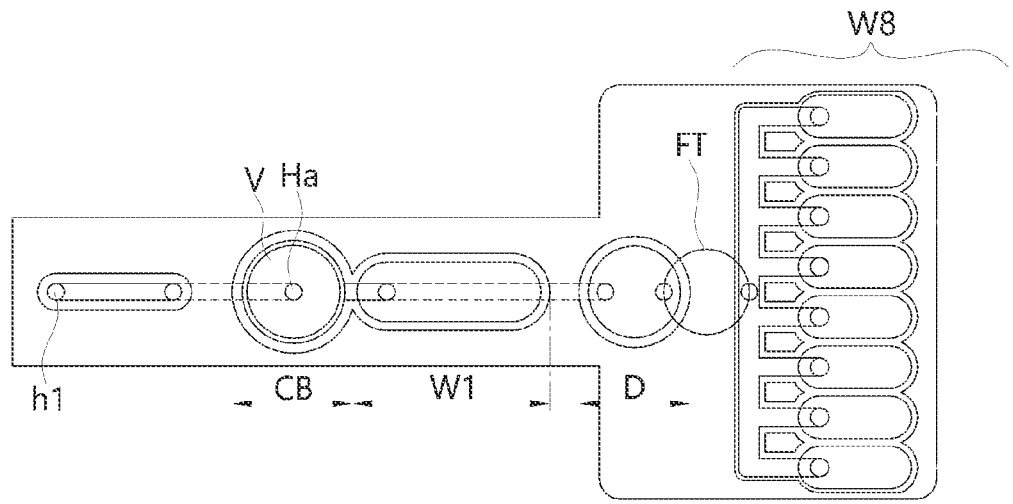
[Fig.13]
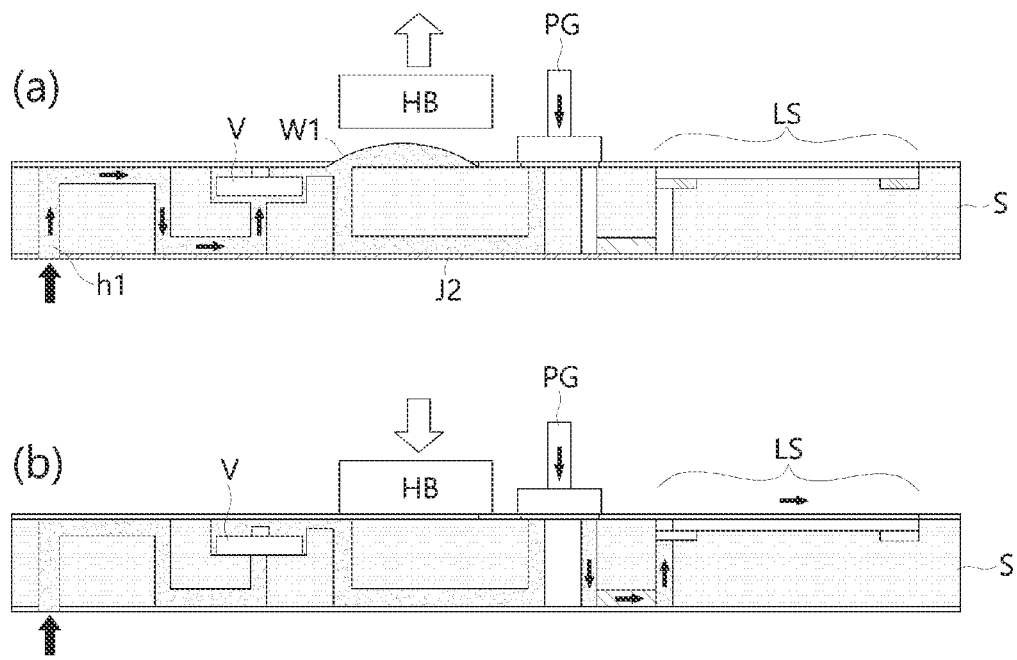

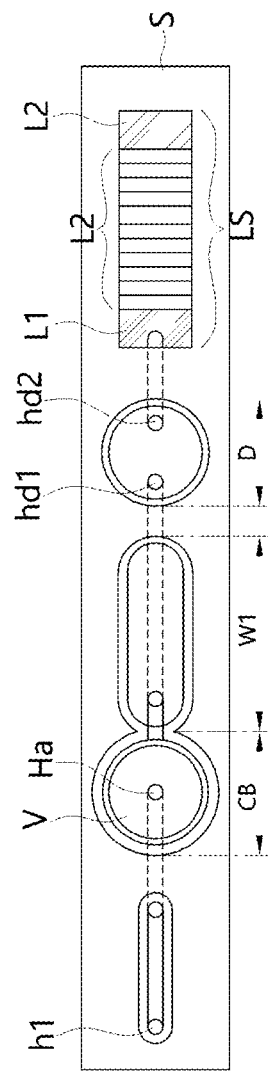

[Fig.15]
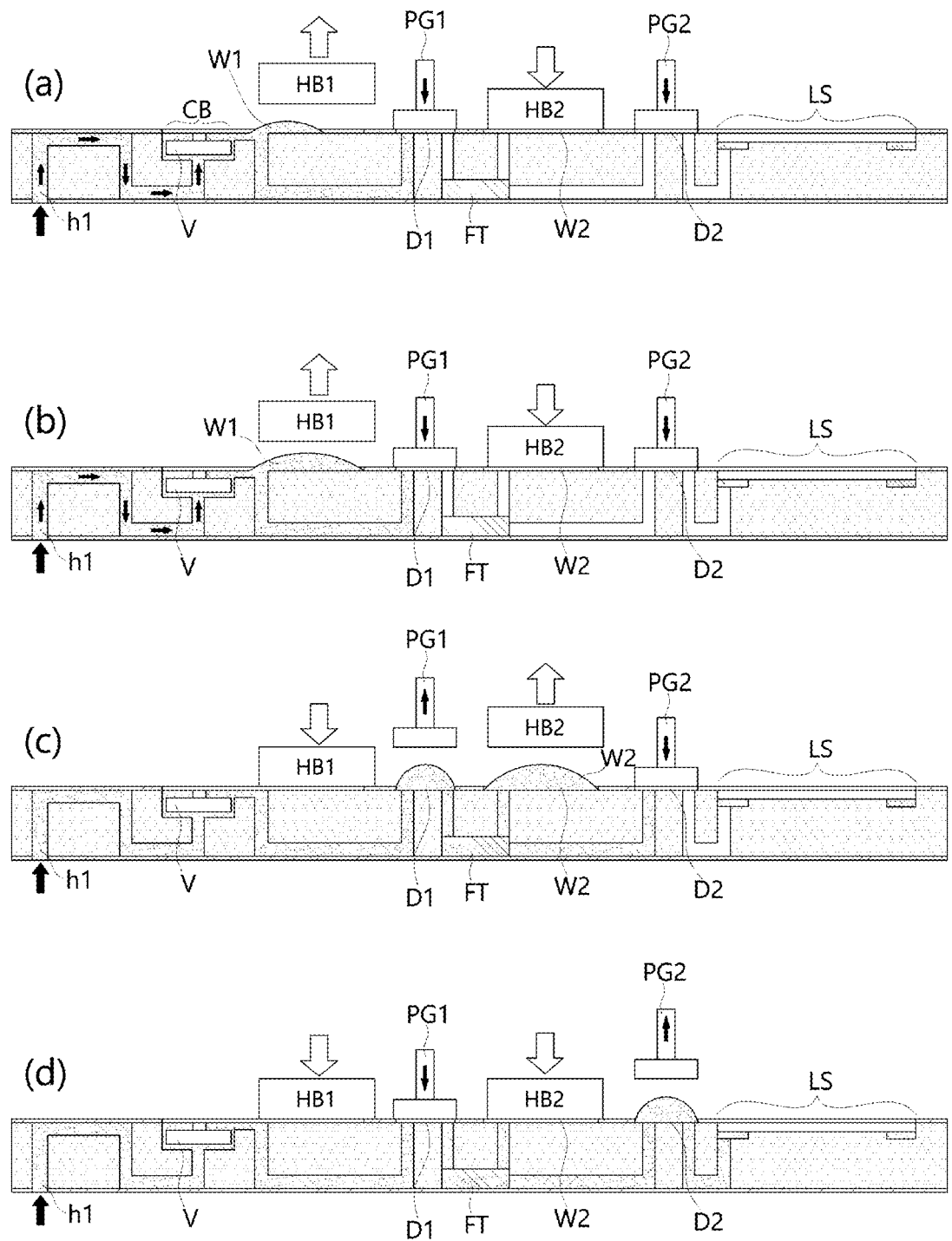

[Fig.16]
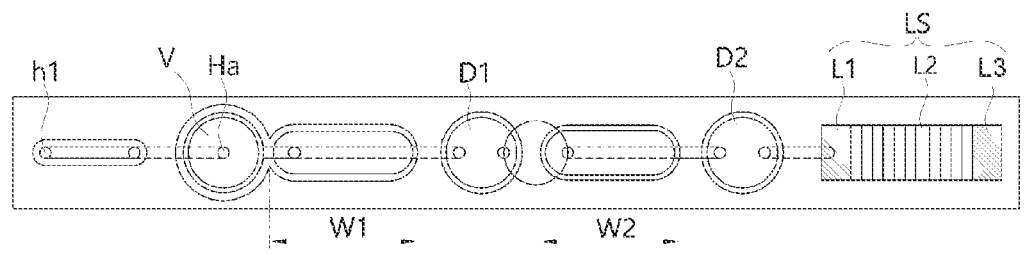
[Fig.17]
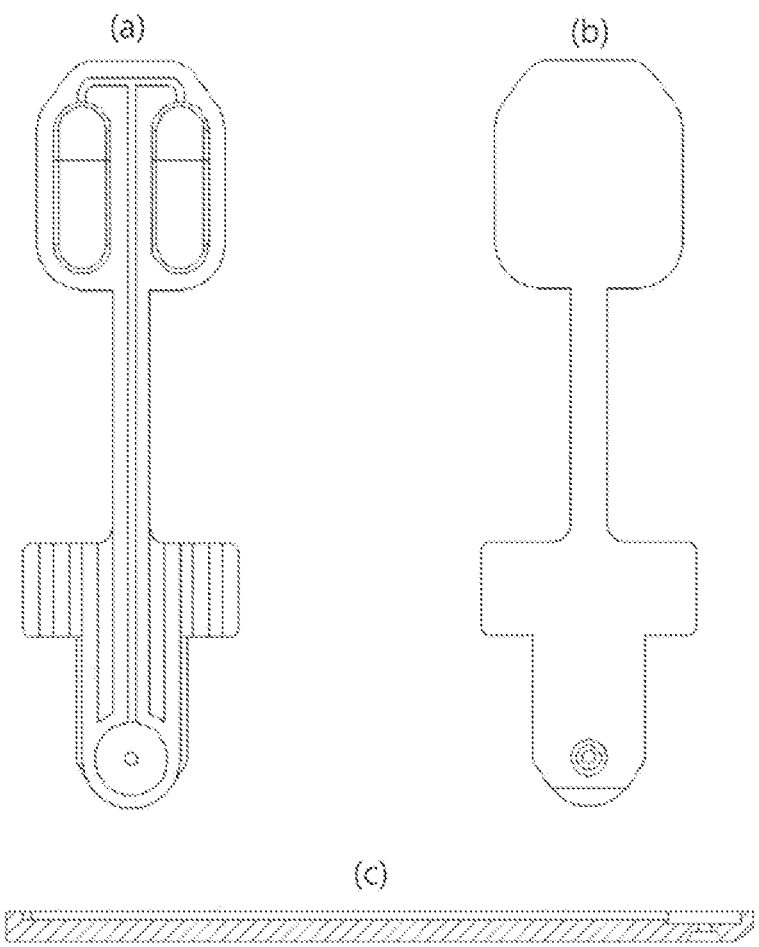

[Fig.18]
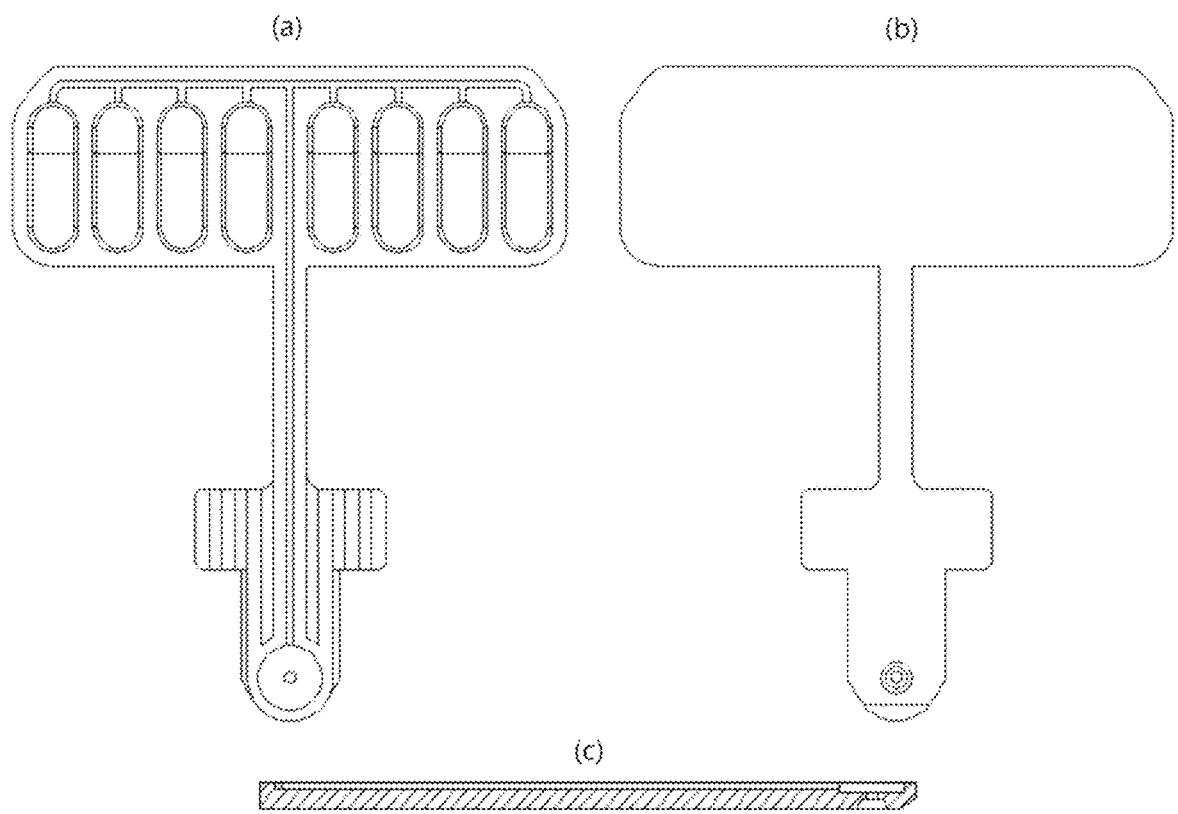

HIGH-SPEED POLYMERASE CHAIN REACTION ANALYSIS PLATE

CROSS-REFERENCE TO RELATED APPLICATIONS

This application is a 371 U.S. National Phase of International Application No. PCT/KR2019/003376, filed Mar. 22, 2019, which claims priority to Korean Patent Application No. 10-2018-0033934, filed Mar. 23, 2018. The entire disclosures of the above applications are incorporated herein by reference.

TECHNICAL FIELD

The present invention relates to a polymerase chain reaction (PCR) analysis plate which is formed by providing a PCR unit, a flow channel, a valve, and a lateral flow analysis unit on a polymer substrate and fusing an elastic film to enable temperature-cycling PCR to be performed at high speed and is capable of quickly transferring heat to a PCR solution through the elastic film. More particularly, the present invention relates to a high-speed PCR analysis plate which, when used, enables a real-time PCR reaction and a real-time nested PCR reaction to be performed and a lateral flow assay using paper with fixed nucleic acid probes and the like to be performed after both PCR reactions and thus is usable for quickly checking the results of target amplification.

BACKGROUND ART

Point-of-care (POC) PCR diagnostic technology capable of quickly diagnosing patients is attracting attention as a very important technology for evidence-based precision medicine and has been greatly advanced due to the development of various nucleic acid markers and high-speed nucleic acid marker detection technologies.

Many nucleic acid marker detection methods used in molecular diagnosis use a polymerase chain reaction (hereinafter referred to as PCR). Since invented by Kary Mullis in 1985, PCR has been able to amplify specific DNA quickly and easily and thereby identify whether a trace amount of specific DNA/RNA is present in a biological sample, and thus has been widely used for diagnosing pathogenic microbial infections such as viral infections. In addition, PCR makes it possible to quantitatively analyze the number of pathogen nucleic acids with high accuracy by a method such as quantitative PCR (qPCR, real-time PCR) and thereby accurately measure the concentration of viruses such as HIV, HCV, and HBV in the blood. Therefore, PCR has been widely used for quantitative molecular diagnosis for monitoring a therapeutic effect or the like.

In order to perform the above-described PCR, it is required that after a nucleic acid extraction process of removing, from a biological sample, materials inhibiting the PCR of the biological sample and extracting pure nucleic acids is performed, a PCR solution containing the extracted nucleic acids and a primer/probe is prepared and input in a reaction vessel, and subsequently, the reaction vessel is subjected to temperature cycling to amplify the target nucleic acids. In addition, in order to quantitatively measure a PCR product, it is required that a fluorescence amount measuring device for measuring, in real-time, the fluorescence generated proportionally to the PCR product being amplified is provided.

In order to quickly identify a patient's infectious pathogen among many pathogens related to clinical symptoms during molecular diagnosis, a multiplex test method capable of simultaneously testing a large number of targets is required. In order to qualitatively detect a large number of targets, it is required that after a multiplex PCR reaction, a real-time nested PCR reaction or a lateral flow assay using paper with various fixed probes is performed.

Recently, through research and development, various automated systems in which the entire processes of nucleic acid extraction, PCR, and reaction product detection processes are automated and which thus allow even people not having a high degree of professional knowledge to easily use PCR and devices using the automated systems have been developed. However, the existing devices are complex, expensive, and still have a long processing time, so there is a demand for a technique capable of quickly and economically performing PCR and quantitatively or qualitatively analyzing a large number of targets in a fully automated manner. More specifically, there is a demand for a novel, economical PCR vessel capable of significantly reducing a PCR temperature-cycling time and quantitatively or qualitatively analyzing a large number of targets.

Although 0.5 ml reaction vessels were used in the early stages of PCR technology development, the PCR equipment commonly and widely used nowadays uses 0.2 ml PCR vessels to reduce a temperature-cycling time. However, when this equipment is used, since it takes about one to two hours to cycle the temperature for PCR, methods enabling faster and more accurate PCR for on-site diagnosis have been continuously developed (Lab Chip, 2016, 16, 3866-3884).

The principle of PCR is as follows. After a DNA double helix is separated into single strands by heating at a temperature of 95° C. or more, a PCR solution is cooled to annealing temperature so that primers contained in the PCR solution, which are complementary to either end of the site to be amplified, are selectively hybridized to the ends, then a reaction in which a DNA polymerase sequentially connects four types of nucleoside triphosphates, A, G, T, and C, in a way that is complementary to each of the single strands and thereby double helices are formed is performed repeatedly. In laboratories, the reaction is caused by performing 30 to 45 cycles (n) of repeated heating and cooling of a PCR solution so that a specific DNA double helix is exponentially amplified to $2^n$ double helices. The PCR for detecting RNA is performed after first synthesizing cDNA using a reverse transcriptase, and the cDNA is amplified through PCR and quantitatively analyzed.

Various methods have been developed to analyze amplified target nucleic acids after PCR. The earliest developed method included separating reaction products according to the size of DNA through electrophoresis which is commonly used in genetics laboratories, and then confirming if the amplified target DNA is DNA of the size of interest. However, this method required an additional complex electrophoresis process after PCR and had a long analysis time, and when the PCR experiment is repeated such as in the case of diagnostic tests, target DNA may leak out and contaminate the laboratory during the electrophoresis process, and this may result in false positives in subsequent PCR experiments. In addition, since final reaction products were analyzed on or after the $30^{th}$ cycle, unlike in the case of fewer types of targets where the targets were continuously amplified until all PCR cycles were completed, when there were many types of target DNA, dNTPs were used up and thus, the amplification reaction was prematurely terminated, making it impossible to quantify initial concentrations of targets through analysis upon completion of PCR cycles.

As a method capable of solving both the quantitation problem and the contamination problem caused by PCR products, a real-time quantitative PCR method has been developed. In the real-time quantitative PCR which is capable of quantitatively analyzing target nucleic acids, materials capable of emitting fluorescence proportionally to the target DNA fragments to be amplified are added to a PCR solution, and then the fluorescence is measured in real-time for each cycle to identify the cycle in which a critical fluorescence level is detected. In this way, it is possible to quantitatively measure initial concentrations of target nucleic acids input into the reaction vessel. As the real-time quantitative PCR method, a method of using a fluorescent dye that emits fluorescence by binding to a DNA double helix to be amplified and a more accurate, fluorescent probe method in which the fluorescent probe emits fluorescence by specifically hybridizing to an amplified nucleic acid sequence have been developed. The method of using a fluorescent probe specific to a nucleic acid sequence has been developed into a powerful technology capable of quantitatively analyzing all of five to six different targets in one reaction solution.

Molecular diagnosis has advanced in the direction of enabling testing of all pathogens causing disease at one time based on clinical symptoms and thereby identifying the exact cause of the disease at one time. Although real-time quantitative PCR is capable of detecting five targets at the same time, since there are many types of pathogens causing similar symptoms such as in the case of respiratory or sexually transmitted diseases, there is a continuously increasing demand for multiplex detection techniques enabling the simultaneous detection of 10 or more or 20 or more targets. As a method of analyzing even a larger number of targets, a multiplex PCR method has been developed. In the multiplex PCR method, a pair of primers capable of amplifying a large number of target DNA are added to a reaction solution and used for amplification. However, since this method may induce non-specific amplification due to the interaction of the primers or the like, an analysis method including an additional verification process has been developed.

As a method for increasing the accuracy of these multiplex tests and conveniently performing the tests at one time, a method of performing multiplex PCR for a large number of targets and then secondarily performing real-time nested PCR using a fluorescent dye has been developed by BioFire Diagnostics (FilmArray®). Although this method provides the convenience of detecting dozens or more targets at the same time, the method has limitations in that it takes about one hour and requires a process for dissolving reagents in water in advance, and is performed using expensive equipment and test kits.

As another method of performing, after multiplex PCR, a hybridization reaction in an array in which various targets are fixed and detecting fluorescence, many methods capable of identifying, using a DNA microarray after PCR, amplified target DNA hybridized with probes attached to specific locations have been developed. Also, a method using 96-well plates including probes fixed to the bottom of the 96 wells has been developed. Although still another analysis method using hybridization with fluorescent barcode beads to which specific DNA probes are attached has been developed by Luminex Corporation, this method has a relatively long analysis time, and the operation is complicated.

As a multiplex target detection method that is less expensive and easier to use, a target nucleic acid detection method capable of performing, after PCR, hybridization using a lateral flow strip, washing, and the like as a single process in about 10 minutes and is economical has been developed (Mao X et al. Anal Chem. 2009 Feb. 15; 81(4):1660-8. doi: 10.1021/ac8024653). In order to commercially test a large number of targets using the same principle, INNO-LiPA™ HPV genotyping kits capable of testing 32 types of genotypes and the like have been developed. However, in the case of such commercial products, since a reaction is carried out for one to two hours using a general PCR tube and then reaction products are tested, manipulation is complicated and time-consuming, and there may be a problem of false positives caused by the contamination of PCR products.

For POC RCR which enables immediate on-site diagnosis, above all, it is necessary to quickly change the temperature of a PCR solution. In addition, in order to selectively amplify only the desired targets through accurate PCR, it is required that primers are designed so as to be specifically hybridized to the desired targets, and it is required that annealing temperature is accurately controlled during PCR temperature cycling.

As described above, many techniques have been developed to thermally cycle a PCR solution at higher speed. The developed methods can be largely classified into methods in which a PCR solution is moved between different spaces and methods in which a PCR solution is subjected to time-difference temperature cycling. In the methods in which a PCR solution is moved between different spaces, a reaction vessel or the reaction solution is moved to and comes into contact with thermoelectric bodies maintained at constant temperatures and is thereby quickly heated or cooled. First, as a way to move the reaction vessel, a method of moving a reaction vessel rack so that the PCR vessel can be repeatedly immersed in a high-temperature water bath and a low-temperature water bath for a predetermined period of time has been developed and implemented as an initial PCR device (Turbo Thermalcycler. Bioneer Corp. Daejeon). The PCR equipment which circulates a reactor between zones of different temperatures as such employs the method of moving a PCR solution between different spaces, and has an advantage in that a liquid of a specific temperature whose temperature has already been accurately maintained comes into contact with, and quickly and accurately transfers heat to, the PCR vessel and causes PCR. However, the PCR equipment has a problem in that since several constant-temperature water baths are required, the equipment is large and requires much work for maintenance and management. For this reason, a method of moving a PCR solution between different aluminum blocks having constant temperatures instead of different liquid baths has been developed (Robo-Cycler® Stratagene, San Diego). However, since this method transfers heat through the contact between solids, there is a problem in that thermal resistance may change due to fine dust, and it is difficult to operate at high speed.

As a method of moving a PCR solution between different spaces for rapid PCR, there have been developed methods of cycling the temperature of a PCR solution by moving the PCR solution between different spaces, which, by allowing only the PCR solution rather than a PCR vessel to quickly move between zones of different temperatures through a microflow channel, enable quick temperature cycling of the PCR solution without the heat capacity of a reaction vessel. These methods can be classified into open reactor methods which allow a PCR solution to flow continuously on a first-in, first-out (FIFO) basis and closed reactor methods which allow a PCR solution to repeatedly move between zones of different temperatures. As the open reactor method, a method of winding a capillary tube around a cylindrical block having compartments with different temperatures and allowing a PCR solution to continuously flow through the capillary tube was developed by Nakano et al. in 1994 (Biosci. Biotech. Biochem., 58(2), 349-352, 1994). In 1998, it was confirmed by Kopp et al. that in PCR equipment with a microflow channel which allows a PCR solution to repeatedly flow between a high-temperature zone and a low-temperature zone, PCR was performed by flowing a 10 µl solution through 20 cycles of 4.5 seconds each (Science 280 1046-1048, 1998).

The PCR method employing a time-difference temperature cycling method is currently adopted by the most widely used PCR equipment in laboratories, and PCR equipment using a time-difference temperature cycling method, which changes temperature over time using a Peltier device or the like in a fixed block, accounts for the majority of such PCR equipment. In order to quickly implement the time-difference temperature cycling method in a fixed reaction vessel, it is required that the reaction solution has a large area of contact with a heat source relative to heat capacity compared to the 0.2 ml reactor generally used in laboratories and that the thermal resistance in the process of transferring heat from the heat source to the PCR solution is low so that the heat is quickly transferred. For this purpose, various PCR vessels having a wide heat exchange area, such as capillary tube-type PCR reactors (e.g., LightCycler 2.0, Roche Life Science), thin plate-type PCR reactors (e.g., GeneXpert, Cepheid), and the like, have been developed. However, these reactors take a long time despite having a large surface area because the reactors heat or cool using air which has low specific heat, and therefore, it may take 30 minutes to perform 35 cycles, and it is relatively difficult to accurately control temperature. In the case of PCR reactors capable of circulating heat at high speed, although a smaller amount of a reaction solution is generally used, due to the fact the less the PCR solution, the smaller the amount of target nucleic acid introduced, it becomes impossible to detect trace amounts of pathogens, and therefore, a limit of detection (LOD) is increased. Therefore, in order to use 10 to 50 µl of a PCR solution commonly used in molecular diagnosis, it is required that the reactor has a relatively large surface area so that heat can be quickly transferred. In this regard, a case where 10 µl of a PCR solution was input in a shallow reaction depression having a size of 17×15 mm and a depth of 40 to 80 µm made on a silicon wafer and was covered with a glass plate to increase a heat-exchange area per unit volume (>100 mm$^2$/10 µl) has been reported. However, in this case, since a conventional Peltier device and an aluminum block were used, the thermal resistance in transferring heat to the reaction solution on the silicon wafer was high, so it took much time to increase or decrease the temperature of the reaction solution, and it merely had the effect of reducing the time taken for one cycle to about three minutes (Clin. Chem. 40/9, 1815-1818 (1994)).

In order to solve the above-described problems, Liat® (Lab-in-a-tube), which employs a method of quickly moving a PCR solution between different spaces and moves the PCR solution between two constant-temperature blocks through a film tube, has been developed. With this method, it is possible to extract nucleic acids and obtain real-time quantitative PCR results in as little time as 15 minutes. However, since a reaction occurs in one vinyl tube in this method, this method has a limitation in testing multiple targets, and since reagents should be input in the tube, this method is less efficient for mass production.

Although various structures enabling POC PCR for on-site molecular diagnostic tests have been continuously invented, an economical multiplex POC PCR reactor enabling quick and fully automated testing of a large number of targets has not yet been developed.

DISCLOSURE

Technical Problem

The present invention is directed to providing a PCR analysis plate which enables the quantitative or qualitative analysis of a large number of targets to be quickly performed on-site through real-time quantitative PCR. In addition, the present invention is directed to providing a plate required for real-time nested PCR, which is capable of quickly detecting trace amounts of targets on-site using the same principle. In addition, the present invention is directed to providing a PCR analysis plate which is capable of performing multiplex PCR to detect multiple targets, performing primer extension chain reactions, and detecting trace amounts of many types of targets through lateral flow assay. The present invention has been devised to solve the above-described problems, and the above-described PCR analysis plates are economical PCR plates which are capable of accurately cycling the temperature of a reaction solution in a short time and are suitable for automated production.

In addition, the present invention is directed to providing a PCR analysis plate which has excellent reproducibility as a PCR dried material in a dried state in a PCR vessel is uniformly mixed with a nucleic acid solution being injected, wherein, in the PCR analysis plate, the dried material in a dried state in a PCR vessel includes a primer, a probe, and one or more of two nucleic acid polymerases, and the PCR analysis plate enables PCR to occur uniformly and effectively by homogeneously dissolving, in a short time, the dried material in a nucleic acid solution extracted from a sample.

In addition, the present invention is directed to providing a PCR plate capable of minimizing false positives by having a structure allowing PCR reactants causing false positives to stay in a closed space without leaking out.

Technical Solution

In one embodiment of the present invention, a plate-type PCR reactor in which an elastic thermal conductive film is fused has been designed in order to provide an economical PCR plate that is capable of accurately cycling the temperature of a PCR solution at high speed, is suitable for mass production, and allows a dried material in a dried state in a PCR vessel to be uniformly mixed with a nucleic acid solution being injected.

A polymer film is fused to an upper surface of the plate into the shape of a closed line including an injection passage and an inlet connected to the injection passage, and thereby a structure in which PCR reactants are sealed with a thin and wide film is formed. When a nucleic acid solution is injected into the inlet, the solution is injected along with air and pushes the air in the channel, and as the elastic film is stretched to form a convex shape, the PCR reactants are disposed inside the plate. Specifically, as the injection of the nucleic acid solution causes a PCR mixture including a primer, a primer/probe, or a primer and a probe, which is in the form of dried material, to be dissolved, reactants for PCR are placed inside the plate. In this case, the reaction vessel may be maintained convex in a state in which positive pressure is applied by a shut-off valve disposed above the injection channel or a check valve for preventing backflow. The shut-off valve may be provided so that it opens when a solution is injected and is closed after the injection so that a PCR unit can maintain positive pressure, and it is preferable that a check valve for preventing backflow is provided so that even after PCR is over, it is possible to prevent the PCR solution from flowing reversely and being discharged and causing contamination. In this case, PCR may be performed by alternately bringing a high-temperature plate and a low-temperature plate into close contact with the elastic film which has become convex due to the solution as described above.

In addition, in order to easily fuse an elastic film to a base substrate using a sealing heater, projections having a uniform height of 1 to 2 mm may be formed on an upper surface of the plate into the shape of the closed lines to be formed on the plate through fusing, and then a polymer film having elasticity may be fused to the projections so that a PCR unit is formed with a structure of a depression having a small depth of 1 mm or less and a large area on a plate.

In one embodiment of the present invention, in order to perform real-time quantitative PCR using the above-described plate, the plate may be formed of a transparent material so that the plate is irradiated with excitation light through a surface, fluorescence is detected, and thereby real-time quantitative PCR is enabled.

In one embodiment of the present invention, in order to provide a plate required for real-time nested quantitative PCR which is capable of quickly detecting trace amounts of targets on-site using the same principle, an additional, second PCR unit of the same form may be provided to the plate by fusing one elastic film to one plate so that PCR units are formed, forming a flow channel connecting one PCR unit to another, and installing a shut-off valve in the middle of the flow channel so that the plate enables a primary PCR reaction and a secondary, real-time nested PCR reaction to be performed.

Further, in one embodiment of the present invention, in order to detect a large number of targets, there is also provided an analysis plate which, by having a plurality of secondary PCR units, a flow channel connecting a primary PCR unit with the plurality of secondary PCR units in parallel, and a shut-off valve, enables a multiplex PCR reaction to be performed in the primary PCR unit and a plurality of secondary, real-time nested PCR reactions to be subsequently performed.

In addition, in order to qualitatively detect a large number of targets using a reactor having the same structure, a PCR analysis plate may be manufactured by forming a primary PCR unit, a secondary reaction unit, and a lateral flow analysis unit on which paper with fixed probes is mounted and forming a flow channel connecting the units and a shut-off valve by fusing the same elastic film to the same plate. When this PCR plate of the present invention is used, a multiplex PCR reaction is performed first, and by opening the shut-off valve, a primer extension reaction using a labeled primer is repeatedly performed 10 or more times as secondary reactions in a second reactor, and by opening a second shut-off valve and passing a solution of labeled, single-stranded DNA through paper for lateral flow assay (hereinafter abbreviated as LFA), a large number of amplified targets are qualitatively analyzed at the same time. In this case, as the label, gold nanoparticles or fluorescent materials may be used.

Advantageous Effects

According to embodiments of the present invention, when a PCR analysis plate of the present invention has advantages in that when a heating block presses air maintaining positive pressure, since the air is compressed and the pressure is further increased, the elastic film in contact with a reaction solution comes into close contact with the heating block with even pressure, and therefore, heat can be reproducibly transferred to the PCR solution with minimal thermal resistance. Therefore, there is an advantage in that since a high-temperature heating block and a low-temperature heating block sequentially come into contact with an elastic film which has become convex due to the PCR solution injected into a reaction unit of the plate, PCR temperature cycling can be performed at high speed. Since the heating blocks have a much larger heat capacity than the PCR solution and maintain constant temperatures, the heating blocks can quickly transfer heat to a large area through the elastic film and change the temperature of the PCR solution. Since it is sufficient if the heating blocks maintain constant temperatures and it is not required to thermally cycle (i.e., heat and cool) the temperatures of the heating blocks themselves, electricity consumption is small, and temperature cycling can be stably controlled.

In addition, since the solution inside the reaction vessel has an air layer exhibiting elasticity, when the part which has become convex due to the PCR solution is pressed, the solution can move inside the PCR vessel. Since a dried primer/probe can be well dissolved due to the movement of the solution, there is an advantage that uniform PCR can be performed.

In addition, since a shut-off valve is provided so that positive pressure is maintained in the reaction space of the plate where reactants, which are PCR amplification products, cause a PCR reaction and a check valve structure having a backflow prevention function is provided so as to prevent, even after PCR is over, the PCR solution from flowing reversely and being discharged and causing contamination, it is possible to provide a reliable reaction plate in which the risk of false positives due to contamination by PCR amplification products is eliminated.

In addition, since a PCR analysis plate of the present invention is formed of a transparent polymer material, it is possible to perform real-time quantitative PCR by irradiating the plate with excitation light through a lower surface and detecting fluorescence which increases with the progress of PCR.

According to the present invention, since an additional, second PCR unit of the same form is provided to the above-described plate by fusing one elastic film onto one plate so that PCR units are formed, forming a flow channel connecting one PCR unit to another, and installing a shut-off valve in the middle of the flow channel, primary PCR and then secondary, real-time nested PCR can be performed, and therefore, real-time nested quantitative PCR capable of quickly detecting trace amounts of targets on-site can be performed.

In addition, according to one embodiment of the present invention, since a plurality of secondary PCR units are installed and a flow channel connecting a primary PCR unit with the plurality of secondary PCR units in parallel and a shut-off valve are provided, it is possible to perform a multiplex PCR reaction in the primary PCR unit and subsequently perform a plurality of real-time nested PCR reactions and thereby detect a large number of targets with high sensitivity.

In addition, when the PCR analysis plate of the present invention having a primary PCR unit, a secondary reaction unit, and a lateral flow analysis unit on which paper with fixed probes is mounted is used, it is possible to perform a multiplex PCR reaction first, and by opening a shut-off valve, repeatedly perform a primer extension reaction using a labeled primer 10 or more times as secondary reactions in a second reactor, and by opening a second shut-off valve, allow a solution of labeled, single-helix DNA to pass through LFA paper with fixed anchor probes, and by identifying attached targets by examining the presence of labels at positions where the probes are fixed, quantitatively detect a large number of targets at the same time at high speed.

According to one embodiment of the present invention, it is possible to provide a PCR plate which enables automated real-time detection of reaction products through the extraction of nucleic acids from biological samples, PCR, and scanning, is capable of performing various tests in one operation, is easy to use, and in particular, is capable of giving accurate results in a short time.

DESCRIPTION OF DRAWINGS

FIG. 1a and FIG. 1b are a set of conceptual diagrams illustrating the operation mechanism of a PCR analysis plate according to one embodiment of the present invention including a shut-off valve and a fused elastic film.

FIG. 2a and FIG. 2b are a set of conceptual diagrams illustrating the operation mechanism of a PCR analysis plate according to another embodiment of the present invention including a check valve and a fused elastic film.

FIG. 3 is a perspective assembly view of the PCR analysis plate of FIG. 2 having a check valve and two PCR units, which shows an elastic film to be fused, the check valve, and a sealing agent for forming a flow channel.

FIG. 4a and FIG. 4b are top and bottom plan views of the PCR analysis plate of FIG. 3, which shows the elastic film to be fused, the check valve, and the sealing agent for forming the flow channel.

FIG. 5 is a cross-sectional view of the PCR analysis plate of FIG. 4 taken along the line A-A'.

FIG. 6a and FIG. 6b show a plan-view photograph (FIG. 6a) and an oblique-view photograph (FIG. 6b) showing the actual appearance of the PCR analysis plate of FIGS. 3 and 4 and shows that the elastic film forms a convex shape in which positive pressure is maintained as a reaction solution is injected into a receiving unit.

FIG. 7 is top and bottom plan views of a PCR analysis plate having a check valve and eight PCR units and a cross-sectional view of the PCR analysis plate taken along the line A-A'.

FIG. 8a, FIG. 8b and FIG. 8c are a set of conceptual diagrams illustrating the operation mechanism of a PCR analysis plate for nested PCR according to the present invention having a check valve, a first PCR unit, and a second PCR unit and enabling nested PCR.

FIG. 9 is a plan view of the PCR analysis plate of the present invention having a check valve, a first PCR unit, and a second PCR unit and enabling nested PCR.

FIG. 10 is a perspective assembly view of the PCR analysis plate for nested PCR of FIG. 8 having a check valve, a first PCR unit, a second PCR unit, a shut-off valve, and a purification unit, which shows an elastic film to be fused, the check valve, the purification unit, the shut-off valve, and a sealing film for forming a flow channel.

FIG. 11 is a lower assembly view of the PCR analysis plate of FIG. 10.

FIG. 12 is a diagram illustrating a PCR analysis plate according to still another embodiment of the present invention.

FIG. 13a and FIG. 13b are a set of conceptual diagrams sequentially illustrating the operation mechanism of a PCR analysis plate of the present invention enabling post-PCR lateral flow analysis.

FIG. 14 is a plan view of the PCR analysis plate of FIG. 13.

FIG. 15a, FIG. 15b, FIG. 15c, and FIG. 15d are a set of conceptual diagrams sequentially illustrating the operation mechanism of a PCR analysis plate of the present invention enabling, after a PCR reaction, an asymmetric PCR reaction or an extension reaction using a nested primer to be performed, followed by lateral flow analysis.

FIG. 16 is a plan view of the PCR analysis plate of FIG. 15.

FIG. 17a, FIG. 17b and FIG. 17c are, respectively, a top plan view, a bottom plan view, and a cross-sectional view of a PCR analysis plate according to yet another embodiment of the present invention having two PCR units.

FIG. 18a, FIG. 18b and FIG. 18c are, respectively, a top plan view, a bottom plan view, and a cross-sectional view of a PCR analysis plate according to yet another embodiment of the present invention having eight PCR units.

MODE OF THE INVENTION

Advantages and features of the present invention and a method of achieving the same will become apparent with reference to the exemplary embodiments described below in detail as well as the accompanying drawings. However, the present invention is not limited to the embodiments described herein and may be embodied into other forms. Rather, the exemplary embodiments introduced herein are provided so that the disclosed contents may be thorough and complete, and that the spirit of the present invention may be sufficiently conveyed to those skilled in the art.

The terms used herein have been used only for the purpose of describing particular embodiments and are not intended to limit the present invention. In the present specification, singular expressions include plural expressions unless the context clearly indicates otherwise. It will be further understood that the terms "comprises," "comprising," "includes," "including," "has," and/or "having," when used herein, specify the presence of stated features, integers, steps, operations, elements, components and/or groups thereof, but do not preclude the presence or addition of one or more other features, integers, steps, operations, elements, components and/or groups thereof.

FIG. 1 is a set of conceptual diagrams illustrating the main parts of a high-speed PCR analysis plate (hereinafter referred to as "PCR plate") according to one embodiment of the present invention. FIG. 2 is a set of conceptual diagrams illustrating a case where a check valve rather than a shut-off valve as in FIG. 1 is provided. FIG. 3 is a perspective assembly view illustrating one example of the PCR plate of FIG. 2 having a check valve and two PCR units, which shows an elastic film to be fused, a check valve, and a sealing agent for forming a flow channel. FIG. 4 is top and bottom plan views of the PCR plate of FIG. 3, and FIG. 5 is a cross-sectional view of the PCR plate of FIG. 4 taken along the line A-A'.

Referring to FIGS. 1 to 4, a PCR plate of the present invention may have a structure including a base substrate S, a reaction unit W which is provided on the base substrate, receives a nucleic acid solution, and includes at least one accommodation region where a PCR mixture including a primer, a primer/probe, or a primer and a probe, which is in the form of dried material, is accommodated, and an elastic film F which seals the inside of the reaction unit W.

Specifically, as in the structure shown in FIG. 3, the PCR plate of the present invention is implemented as a plate-shaped structure including one surface portion and the other surface portion opposite to the one surface portion.

Here, in the one surface portion, there is provided a reaction unit W which implements accommodation regions W1, W2 for accommodating a PCR mixture including a primer, a primer/probe, or a primer and a probe, which is in the form of dried material and, by receiving a nucleic acid solution injected by a nucleic acid extraction cartridge or an external injection device, realizing PCR. The reaction unit W may be implemented as a structure in which an elastic film F is fused to the base substrate S, and according to one exemplary embodiment of the present invention, the reaction unit W may also be implemented as an isolated space as shown in FIG. 4 using a projecting partition wall GA having a height of 2 to 4 mm, preferably 2 to 3 mm, and more preferably 2 mm or less. When the partition wall is implemented with a height of more than 4 mm, there is a disadvantage in that when a high-temperature heating block and a low-temperature heating block come into contact with the elastic film at a later time point, temperature (heat) is not precisely transferred to reactants at the bottom. It is most preferred that the partition wall is implemented with a height of 2 mm or less, and even when the reaction unit is implemented through fused regions, it is preferred that the fused regions are implemented with a height (thickness) of 2 mm or less.

In addition, in the following embodiments of the present invention, the concept of "fusing" is defined as a state in which a film material is in close contact with a base substrate without any lifting, and although the definition generally refers to the fusing achieved by ultrasonic waves, heating, pressing, or the like, it is considered that the concept also includes modifications of close contact implemented using a predetermined adhesive material or attachment.

In addition, in implementing the reaction unit W, although FIG. 3 illustrates the implementation of two accommodation regions W1, W2 and FIG. 7 illustrates the implementation of eight accommodation regions, the present invention is not limited thereto, and of course, it is also possible to implement the reaction unit W as a structure having more than one or two accommodation regions.

In addition, the PCR plate of the present invention may be formed by fusing an elastic film F having elasticity onto the reaction unit W into the shape of a closed line and may be implemented as a structure which seals the inside of the accommodation regions. Hereinafter, in the present invention, the expression "having the shape of a closed line" defines a processed structure in the form of a fused linear region in which when predetermined outer edge portions of an elastic film are fused to a base substrate, since the fused regions are fused to the base substrate perfectly, the structure is implemented as a structure in which the fused regions and the inside space are sealed.

The elastic film F is disposed on the base substrate S such that the elastic film F seals all of the accommodation regions W1, W2, a flow channel unit J, and a valve unit to be described below.

As illustrated in FIG. 3, the partition wall GA implements the accommodation regions W1, W2 and the flow channel unit J connected to the accommodation regions W1, W2. The flow channel unit J is capable of guiding the nucleic acids injected through an injection hole h1 formed at one end of the base substrate opposite the accommodation regions W1, W2 to the accommodation regions W1, W2 via a check valve depression K.

In this case, a PCR mixture including a primer, a primer/probe, or a primer and a probe, which is in the form of dried material for realizing PCR and is accommodated in the accommodation regions W1, W2, reacts with the injected nucleic acids, causing a PCR reaction.

In order to realize high-speed PCR, a process of alternately bringing high- and low-temperature heating blocks HB into close contact with upper portions of the accommodation regions W1, W2 is required so that the temperature conditions capable of inducing PCR can be applied. In this case, heat transfer is affected by how close the heating blocks HB come into contact with the elastic film F.

According to one embodiment of the present invention, since the elastic film forming the accommodation regions W1, W2 of the PCR plate 200 is stretched to form a convex shape by the injection of a solution, when the heating blocks come into close contact with the convex part of the elastic film surface, the elastic film forms uniform close contact with the heating blocks HB, and a rapid PCR reaction is enabled.

In addition, when the elastic film F having a convex shape due to the injected solution is pressed, since the nucleic acid solution injected from the outside is moved and homogeneously mixed with a PCR mixture including a primer, a primer/probe, or a primer and a probe, which is in the form of dried material, accommodated in an accommodation region, a PCR reaction is uniformly implemented.

However, when pressure is applied on the upper surface of the accommodation regions W1, W2 by the heating blocks HB as shown in FIG. 2, a phenomenon in which reactants undergoing a mixed reaction again flow reversely through the flow channel unit J occurs. Accordingly, in order to prevent the backflow, the valve units are provided in the present invention, and a shut-off valve D (FIG. 1) or a check valve V (FIG. 2) for preventing the backflow of a solution pushed out by the heating blocks is disposed on the base substrate.

In one embodiment of the present invention, the "shut-off valve" is configured as a part that performs an intermittent function of blocking or applying the flow of a fluid on a base substrate, and is defined, in the structure of FIG. 10, as the concept of a region D implemented by a pair of holes hd1, hd2 realizing the introduction of a fluid into the base substrate S and the elastic film member F provided on top. In addition, the check valve V is an independent structure implemented between the elastic film and the base substrate and is defined as a structure that controls the flow of a fluid.

In addition, according to one exemplary embodiment of the present invention, the PCR plate includes all structures having one or more of a shut-off valve D disposed between a flow channel unit J connected to an inlet of a reaction unit W and the reaction unit W and a valve unit including a check valve V for preventing the backflow of a solution injected into the reaction unit W and the flow channel unit J connected to the inlet of the reaction unit W.

That is, in one embodiment of the present invention, the above-described check valve V is implemented in the valve unit portion of FIG. 3 and seated so as to be spaced from the inside of the check valve depression K communicating with one end of the flow channel unit J communicating with the reaction unit W.

The check valve V may be operated to close a fluid inlet hole Ha for introducing fluid into the valve unit by floating.

To describe functions of the check valve V of the present invention in detail, as shown in FIGS. 2 to 4, in the PCR plate of the present invention, the injection path for injecting nucleic acids into the reaction unit W is applied through the injection hole h1 provided at one end of the plate, and the applied nucleic acids pass through the check valve depression K and the flow channel unit again and move toward the rear end of the PCR plate to the reaction unit W.

The "backflow" phenomenon refers to a process in which reactants inside the accommodation region flow in the reverse direction of the injection path and are discharged to the outside. In the present invention, the "backflow" phenomenon may occur when an injected nucleic acid solution flows through the flow channel, causing the air in the flow channel to be compressed and the elastic film to be stretched to form a convex shape and thereby form positive pressure, when a convex elastic film part of the accommodation region is pressed and a dried material in the accommodation region is mixed with the solution, or when additional positive pressure is formed inside the accommodation region by the heating blocks alternately applying high temperature and low temperature to a convex elastic film part of the accommodation region for PCR, in which case, reactants inside the accommodation region flow in the reverse direction of the injection path and are discharged to the outside.

FIG. 5 is a cross-sectional view of the PCR plate of FIG. 4 taken along the line A-A', and FIGS. 1 and 2 are conceptual diagrams illustrating operation mechanisms of PCR plates according to embodiments of the present invention.

Hereinafter, the operation mechanism of a PCR plate having a structure having a check valve as implemented in one embodiment of the present invention will be described with reference to FIGS. 3 to 5.

As shown in FIG. 5, in the PCR plate according to one embodiment of the present invention, a fluid inlet hole Ha through which a nucleic acid fluid introduced from the outside is injected may be disposed below a check valve depression K where a check valve V is placed, and a path-forming block Va structure for ensuring a fluid movement path may be implemented below the fluid inlet hole Ha.

In the PCR plate, a fluid containing nucleic acids introduced from the outside is injected into the injection hole h1 through the bottom of the plate, and the injected fluid moves to the check valve depression K through an inflow path.

Hereinafter, the above-described operation will be described in detail with reference to FIG. 2.

FIG. 2 is a set of conceptual diagrams illustrating a process in which a fluid containing nucleic acids moves to a reaction unit W in a PCR plate structure.

Referring to FIG. 2, when a fluid containing a nucleic acid extract is introduced from the outside through the injection hole h1, the fluid moves along a path (in the direction indicated by the arrows) from the bottom of the fluid inlet hole Ha toward the check valve depression K, thereby causing the check valve V to slightly float (FIG. 2A).

Subsequently, as the elastic film slightly stretches due to the pressure caused by the injection of the fluid containing a nucleic acid extract, the check valve V floats, and the fluid containing a nucleic acid extract moves easily to the reaction unit W, and after moving, the fluid reacts with a PCR mixture including a primer, a primer/probe, or a primer and a probe, which is in the form of dried material and has already been provided in the reaction unit W, that is, an accommodation region, and thereby PCR is performed (FIG. 2B).

In this case, the pressure on the inside of the elastic film sealing the upper portion of the accommodation region is increased due to the injection of the fluid, causing the surface to convexly bulge out as shown in FIG. 2B. The surface of the elastic film under the influence of positive pressure as such may effectively bring the solution in the reaction unit of the PCR plate into close contact with the heating blocks HB as will be described below, and this may be advantageous for securing precise temperature conditions.

Subsequently, when equipment which is capable of applying a temperature required for a thermal denaturation process and an exact temperature required for an annealing process and performing heating and pressing applies pressure on the inside of the reaction unit (accommodation region) periodically while controlling temperature as required for a PCR process to induce PCR, positive pressure (PP) is formed inside the accommodation region, and reactants are homogeneously mixed.

At the same time, the positive pressure causes a backflow phenomenon in which the mixed reactants are pushed out of the accommodation region reversely.

When such a backflow phenomenon occurs, the check valve V is pressed downward as shown in FIG. 2B, in which case, the check valve V naturally blocks the fluid inlet hole Ha. When the check valve V blocks the fluid inlet hole Ha as such, reactants inside the accommodation region cannot flow reversely to the outside and continue to completely react in the accommodation region.

Therefore, in one embodiment of the present invention, the check valve V is implemented as a three-dimensional structure having an upper surface having irregularities and a lower surface enabling close contact.

That is, the lower surface of the check valve blocks the inlet by coming into close contact with the inlet, and the irregularities on the upper surface face the inner surface of the elastic film, in which case the check valve is pressed, and when a solution is applied to an upper portion of the check valve excluding the irregularities and thus positive pressure is applied, the check valve strongly seals the area around the inlet.

In other words, a structure is implemented so that the check valve V in the check valve depression K floats and opens due to the inflow of the fluid introduced into the reaction unit W, and at the same time, the lower surface of the check valve V is capable of closing the fluid injection hole, and in the upper surface of the check valve V, only the center part comes into close contact with the elastic film, and the remainder comes into contact with the solution.

In this case, although the check valve may be implemented in various structures, materials, and shapes, the structure, material, or shape of the check valve may be variously changed, and for example, the check valve may have the shape of a cone, a two-tier cylinder in which a top diameter is no more than ½ of a bottom diameter, or a cylinder having projections formed on an upper surface thereof. However, it is preferred that the entire lower surface V2 of the check valve is formed of an elastic material such as silicone rubber so that the check valve can efficiently close the entire fluid inlet hole Ha.

FIG. 6 shows actual photographs of a PCR plate implemented according to FIGS. 2 and 5, and FIG. 6A is an image of the PCR plate before injecting a fluid containing nucleic acids, and FIG. 6B is an image of the PCR plate after injecting a nucleic acid solution, which shows that the elastic film in the accommodation region has a convex shape due to the positive pressure applied by the injection of the reaction solution. When high- and low-temperature heating blocks maintaining constant temperatures alternately press the surface of the elastic film having an upwardly convex shape as shown in FIG. 6B, since the convex surface of the elastic film of the accommodation region is pressed, heat is transferred, and as the reaction solution is moved, the PCR solution is uniformly mixed. The backflow caused by the additional pressure applied due to the contact may be controlled through the check valve.

The PCR plate is usable for the analysis of real-time PCR amplification. In order to perform a real-time PCR reaction, a fluorescence value from the PCR unit is measured each cycle, a cycle in which fluorescence is increased above a threshold fluorescence value is identified, and thereby the concentration of a target is measured.

In order to accomplish the above-described objectives, according to one exemplary embodiment of the present invention, the base substrate may be made of a transparent synthetic resin. One example of the transparent synthetic resin is a polymer based on polyethylene (PE), polypropylene (PP), polyester (PET), polycarbonate (PC), or polymethacrylate (PMMA). In addition, it is required that the transparent synthetic resin is a polymer not containing a fluorescent material so that various fluorescent materials used for real-time quantitative PCR can be measured.

Hereinabove, the operation principle of the simplest example of the PCR plate which is the basis of the present invention has been described in detail.

The above-described embodiment is an example of performing a single PCR reaction, and in the present invention, there are additional embodiments for achieving high performance while using the above-described basic principle.

The following is one exemplary embodiment and is an application example relating to the performance of nested PCR which is known as the most efficient method for amplifying trace amounts of targets in a sample containing nucleic acid materials having complex nucleic acid sequences.

FIG. 8 is a set of conceptual diagrams illustrating a PCR plate of the present invention enabling nested PCR and illustrating the operation mechanism of the PCR plate having a check valve, a first PCR unit, and a second PCR unit. FIG. 9 is a plan view of the PCR plate of the present invention of FIG. 8 having a check valve, a first PCR unit, and a second PCR unit and enabling nested PCR.

FIG. 10 is an exploded perspective view illustrating the assembly of the PCR plate of FIGS. 8 and 9.

First, referring to FIGS. 9 and 10, the PCR plate according to the present embodiment of the present invention is implemented to include a pair of reaction units, which are spaced apart from each other, on a base substrate S. That is, a first PCR unit W1 and a second PCR unit W2 are provided. In particular, the first PCR unit W1 and the second PCR unit W2 are implemented as spaces formed by fusing an elastic sealing film, and between the first PCR unit W1 and the second PCR unit W2, a shut-off valve D for controlling the flow of a fluid in a second flow channel unit J2 connecting an outlet of the first PCR unit W1 and an inlet of the second PCR unit W2 is disposed.

That is, the present embodiment of the present invention is different from the embodiment illustrated in FIGS. 2 to 4 including the above-described check valve in that the structure according to the present embodiment has the structure of FIG. 3 but further includes a second PCR unit, a flow channel J2 connected to the first PCR unit W1, and a shut-off valve D for controlling the flow of a solution midway through the flow channel.

In order to improve the efficiency of secondary nested PCR, a purification unit FT containing an absorbent for removing inhibitory materials inhibiting the secondary nested PCR, such as primers and pyrophosphate generated in the primary PCR, may be added to a flow channel before the second PCR unit W2. The second PCR unit W2 is manufactured in the same manner as the first PCR unit W1. The second PCR unit W2 is manufactured by fusing an elastic film to the base substrate into the shape of a closed line including an inlet, wherein, before sealing by fusing the elastic film, additional primers, probes, deoxynucleoside triphosphates (dNTPs), and a polymerase required for the nested PCR are added to the base substrate in the form of dried materials.

FIG. 10 is an overall assembly view of a nested PCR plate. FIG. 11 is a lower assembly view of the nested PCR plate of FIG. 10.

In order to manufacture the nested PCR plate of the present invention, a flow channel on the lower surface of the base substrate S and a purification unit FT containing an absorbent are formed by turning over the base substrate S so that the lower surface thereof faces upward and placing the absorbent in the purification unit FT and sealing with a film F3, and therefore, the flow channel and the purification unit are formed at one time.

Subsequently, after turning over the base substrate S so that the upper surface thereof faces upward, a check valve V is installed, a first PCR dried material and a second PCR dried material are placed in their respective positions in the first PCR unit W1 and the second PCR unit W2, and the elastic film F is fused, and thereby a nested PCR plate of the present invention is obtained.

The absorbent is a porous particle allowing penetration of molecules depending on the sizes of molecules and allows the penetration of small molecules such as primers or pyrophosphate while blocking the penetration of amplified DNA with a large molecular size, which is a product of PCR. As the absorbent, a combination of Sephadex® (G-25 or G-50), porous ceramics, and the like may be used.

The operation principle of the primary PCR of the present invention may be described as follows based on the structure of FIG. 10 with reference to the cross-sectional conceptual diagrams of FIG. 8.

As shown in FIG. 8A, it is required that the shut-off valve is kept closed at all times until the primary PCR is completed. A nucleic acid extract or the like injected through the injection hole h1 passes through the check valve V, and the primary PCR is performed in the first PCR unit W1. While the primary PCR is performed, the check valve V is in a closed state as shown in FIG. 8B and prevents the backflow of reactants. The primary PCR is performed by alternately pressing the bulged part of the elastic film of the first PCR unit W1 with heating blocks HB1.

Subsequently, when the primary PCR of the introduced reactants is terminated, the piston PG pressing the shut-off valve D is raised as shown in FIG. 8C, allowing the solution contained in the first PCR unit W1 under positive pressure to move along the flow channel, pass through the shut-off valve D and then the purification unit FT, and reach the second PCR unit W2.

In this case, in order to move as much entire solution as possible, the solution is pressed with the front heating block HB1 while the rear heating block HB2 is in a lifted state so that the solution is moved completely, and then the shut-off valve D is pressed with the piston to block the flow channel.

Subsequently, the solution is alternately pressed with high- and low-temperature heating blocks HB2, which forms PCR cycles where the amplified products of primary PCR are subjected to a PCR reaction. In this case, in order to perform a real-time PCR reaction, a fluorescence value from the PCR unit is measured each cycle, a cycle in which fluorescence is increased above a threshold fluorescence value is identified, and thereby the concentration of a target is measured. Therefore, it is required that the PCR plate is manufactured using the above-described transparent polymer materials.

FIG. 12 is a diagram illustrating a PCR plate according to still another embodiment of the present invention.

The structure of FIG. 12 is one example of a PCR plate of the present invention which enables multiplex nested PCR for analyzing a large number of targets to be performed.

That is, in various embodiments of the present invention, structures enabling a primary PCR reaction and then a plurality of secondary real-time PCR reactions are implemented.

The structure of FIG. 12 is one example of implementing the gist of the present invention, and FIG. 12 is a plan view of an exemplary PCR plate enabling a primary multiplex PCR reaction and then secondary real-time PCR reactions in eight secondary reaction units to be performed.

That is, the structure of FIG. 12 has the same basic structure as the structure of FIGS. 9 and 10 in the way an injection hole, a check valve, a first PCR unit W1, and a shut-off valve D are arranged and the first PCR unit W1 is configured. However, the structure of FIG. 12 is different from the structure of FIGS. 9 and 10 in that the second PCR unit is implemented as multiple units rather than as a single unit. Therefore, the structure of FIG. 12 is the same as the structure of FIGS. 9 and 10 in terms of operation principle and different in that the flow channel provided after the purification unit FT is formed such that eight secondary PCR units W8 are connected in parallel. The structure of FIG. 12 operates according to the above-described process and has the advantage of being able to analyze a large number of targets through real-time PCR at the same time.

FIG. 13 is a set of diagrams illustrating the structure of a PCR plate according to yet another embodiment of the present invention enabling post-PCR lateral flow analysis. FIG. 14 is a plan view of the PCR plate of FIG. 13.

Referring to FIGS. 13 and 14, since the PCR plate according to the present embodiment of the present invention has a sealed system formed by fusing films F to upper and lower surfaces of a base substrate S made of a polymer, amplification can be completed in a short time, and therefore, the PCR plate is ideal for lateral flow analysis integrated with PCR carried out by, after PCR, passing PCR products through the paper in which nucleic acid probes are fixed to respective bands and analyzing the bands thus hybridized.

Specifically, in order to perform lateral flow analysis after PCR using amplified PCR products, it is necessary that single-helix DNA is finally produced. To this end, when preparing the above-described PCR dried material, a dried material containing an excessive amount of one primer is prepared. When an asymmetric PCR reaction is performed using this PCR material, a PCR product containing an excessive amount of only one strand is finally produced. (Wooddell, C I; Burgess, R (1996). "Use of Asymmetric PCR to Generate Long Primers and Single-stranded DNA for Incorporating Cross-linking Analogs into Specific Sites in a DNA Probe" (PDF). Genome Res. (6): 886-892).

The plate for post-PCR lateral flow analysis according to the present invention is manufactured to be the same as the PCR plate of FIGS. 9 and 10 in terms of having a structure including a check valve, a first PCR unit W1, and a shut-off valve D and in the way the plate is operated. However, the plate for post-PCR lateral flow analysis according to the present invention is manufactured by completing a lower flow channel of the base substrate with a sealing agent, installing the check valve above the lower flow channel and placing the above-described asymmetric PCR dried material and a lateral flow analysis module (LSM) in respective positions, and then fusing an elastic film.

Here, the lateral flow analysis module (LSM) used is a paper module in which a loading pad L1 is attached to a front end and an absorption pad L3 is attached to a rear end and which has bands L2 including a large number of probes fixed thereon in a middle portion of the paper.

In this case, the base substrate S is preferably implemented to include a depression so that the lateral flow analysis module can be seated therein. According to the present invention, it is possible to manufacture a PCR lateral flow analysis plate which enables, by a simple process, a PCR reaction to be performed in a confined space at high speed and lateral flow probe hybridization analysis to be performed.

As shown in FIG. 13, the working principle of the PCR of the present embodiment is basically the same as that of the plate having one PCR unit. However, it is required that the shut-off valve D is kept closed at all times until the PCR is completed. When PCR is terminated, the piston PG pressing the shut-off valve D is raised, causing the solution contained in the PCR unit under positive pressure to move along the flow channel, pass through the shut-off valve D, and enter the lateral flow analysis unit LS. In this case, in order to move as much entire solution as possible, the convex part of the reaction unit is pressed with the heating block HB and thus, the solution is moved. Subsequently, the solution is absorbed by the loading pad L1 and slowly moves along the paper in which probes are fixed in the form of bands L2 and finally reaches the absorption pad L3, and when the solution encounters probes complementary to the targets, since hybridization occurs, the movement of the solution is stopped, and the color of the fluorescent label or gold nanoparticles appears. Through this, various targets can be qualitatively detected. In this case, the temperature of the PCR plate should be kept constant so that hybridization can occur accurately. For this, the temperature of the metal plate on which the PCR plate is placed should be controlled to be constant, and by pressing the heating block HB down while adjusting the temperature of the heating block HB to the same temperature and pressing the shut-off valve with the piston, the temperature of the PCR plate is kept constant.

FIG. 15 is a set of conceptual diagrams sequentially illustrating the operation mechanism of a PCR plate of the present invention enabling, after a PCR reaction, a nested asymmetric PCR reaction or an extension reaction using a nested primer to be performed, followed by lateral flow analysis. FIG. 16 is a plan view of the PCR plate of FIG. 15.

This structure has the most complex form among the structures derived from the present invention and enables a primary PCR reaction, a secondary, nested asymmetric PCR reaction, and then lateral flow analysis to be performed. For this, a first shut-off valve D1 for transferring a solution carrying products of the primary PCR reaction to the secondary PCR reaction and a second shut-off valve D2 for moving a solution from the secondary PCR reaction to a lateral flow analyzer LS are installed.

In addition, a purification unit FT for removing materials inhibiting the secondary PCR reaction from the products of the primary PCR reaction is provided in the flow channel after the first shut-off valve.

As the secondary PCR reaction, a nested asymmetric PCR reaction, a nested primer extension reaction, or the like may be used. In this case, a primer for forming a single helix should be labeled with fluorescence or the like, and a dried material including the primer should be input in the second reaction unit.

In order to manufacture the PCR analysis plate of the present invention, a flow channel on the lower surface of the base substrate and a purification unit containing an absorbent are formed by turning over the base substrate so that the lower surface thereof faces upward and placing the absorbent in the purification unit and sealing with a film, and therefore, the flow channel and the purification unit are formed at one time. Subsequently, after turning over the base substrate so that the upper surface thereof faces upward, a check valve, a first PCR dried material, a second PCR dried material, and a lateral flow module are placed in their respective positions, and an elastic film is fused, and thereby the nested PCR lateral flow analysis plate of the present invention is obtained. The absorbent is the porous particle described above, and as the absorbent, a combination of Sephadex® (G-25 or G-50), porous ceramics, and the like may be used.

Referring to FIGS. 15 and 16, the operation principle of the primary PCR reaction of the present invention is as follows:
  (a) It is required that the first shut-off valve D1 and the second shut-off valve D2 are kept closed at all times until the primary PCR reaction is completed.
  (b) The primary PCR reaction is performed in the reaction unit by the operation of the check valve V as described above in the embodiment of FIG. 9.
  (c) Subsequently, when the primary PCR reaction is terminated, the piston PG1 pressing the first shut-off valve D1 is raised, allowing the solution contained in the first PCR unit under positive pressure to move along the flow channel, pass through the first shut-off valve D1 and then the purification unit FT, and reach the second PCR unit W2. In this case, in order to move as much entire solution as possible, the solution is pressed with the front heating block1 HB1 while the rear heating block HB2 is in a lifted stated so that the solution is moved completely, and then the first shut-off valve D1 is pressed with the piston PG1 to block the flow channel. Subsequently, the solution is alternately pressed with high- and low-temperature heating blocks HB2, which forms secondary PCR cycles, and thereby a secondary PCR reaction is performed. In this case, both the first shut-off valve D1 and the second shut-off valve D2 should be in a closed state.
  (d) After the secondary PCR reaction is terminated, the second shut-off valve D2 opens by displacing piston PG2 to allow the secondary PCR solution to flow to a loading pad of the lateral flow analysis unit LS. When single-helix DNA strands generated in the secondary PCR reaction encounter target probe nucleic acids and stop moving, the targets can be detected by way of detecting labels in each band.

Although the present invention has been described based on specific embodiments thereof, it should be obvious to those of ordinary skill in the technical field to which the present invention pertains that the technical spirit of the present invention is not limited to the embodiments, that modifications or changes may be made within the scope described in the claims, and that such modifications or changes are encompassed within the scope of the following claims.

DESCRIPTION OF REFERENCE NUMERALS

S: base substrate
W: reaction unit
F: elastic film
W1: first PCR unit
W2: second PCR unit
W3: third PCR unit
J: flow channel unit
J2: second flow channel
J3: third flow channel
V: check valve
Va: path-forming block
K: check valve depression
Ha: inlet hole
D, D1, D2: shut-off valve
LS: lateral flow analysis unit
HB. HB1, HB2: heating block
FT: purification unit
h1: injection hole
hd1, hd2: hole
L1: loading pad
L2: band with fixed probe
L3: absorption pad

The invention claimed is:

1. A real-time polymerase chain reaction (PCR) analysis plate device comprising:
  a base substrate in which a first inlet is formed;
  a reaction unit formed as a closed structure on the base substrate with a elastic sealing film fused into the base substrate in a shape of a closed line including the first inlet;
  a first shut-off valve provided between the reaction unit and a first flow channel unit connected to the first inlet of the reaction unit; and
  a first heating block and a second heating block both positioned above the reaction unit, that can move up and down relative to the reaction unit, and are configured to perform heating and pressing,
  wherein the first shut-off valve is configured to be opened by injection of a target nucleic acid solution, and configured to be closed by a piston after the injection of the target nucleic acid solution,
  wherein the piston is positioned above the reaction unit, and
  wherein by the injection of the target nucleic acid solution, the elastic sealing film disposed on the upper portion of the reaction unit is configured to be stretched to form an upwardly convex shaped portion due to positive pressure, and the upwardly convex portion of the elastic sealing film of the reaction unit is configured to be subsequently pressed by the first heating block and the second heating block sequentially to compress the upwardly convex portion and heat the nucleic acid solution by heat transfer via a compressed convex shaped portion of the elastic sealing film to enable a PCR reaction.

2. The real-time PCR analysis plate device of claim 1, comprising:

a first PCR unit and a second PCR unit spaced apart therefrom, which are formed as closed structures by the elastic sealing film being fused into a shape of a closed line, wherein the first PCR unit and the second PCR unit are coupled with each other through a second flow channel unit formed in a lower portion of the base substrate, wherein the first shut-off valve is configured to intermittently control a flow of a fluid in the second flow channel unit between the first PCR unit and the second PCR unit.

3. The real-time PCR analysis plate device of claim 2, wherein:

the second PCR unit is formed by the elastic sealing film being fused into shapes of closed lines forming a plurality of second PCR sub-units having a plurality of second inlets; and the second flow channel unit starts at an outlet of the first PCR unit and branches off at a branching point into a plurality of sub-unit flow channels connected in parallel to the plurality of second inlets of the plurality of second PCR sub-units.

4. The real-time PCR analysis plate device of claim 2, further comprising:

a lateral flow analysis unit disposed to be spaced apart from the second PCR unit, wherein the lateral flow analysis unit includes a third inlet, wherein the lateral flow analysis unit includes a lateral flow analysis module with a fixed nucleic acid probe, wherein the lateral flow analysis unit is formed by the elastic sealing film fused into a shape of a closed line, and wherein the second PCR unit includes a second outlet;

a third flow channel unit connecting the second outlet of the second PCR unit and the third inlet of the lateral flow analysis unit; and a second shut-off valve configured to intermittently control a flow of the target nucleic acid solution into the third flow channel unit.

5. The real-time PCR analysis plate device of claim 2, wherein, in the second PCR unit, a PCR mixture for nested PCR including a dried primer/probe or a dried primer and a fluorescent dye for DNA detection is configured to be applied.

6. The real-time PCR analysis plate device of claim 1, further comprising:

an outlet formed at one end of the reaction unit on the base substrate;

a lateral flow analysis unit coupled to the outlet through a second flow channel unit connected to the outlet, wherein the lateral flow analysis unit includes a lateral flow analysis module with a fixed nucleic acid probe and a second inlet and is formed by the elastic sealing film fused into a shape of a closed line, and wherein the first shut-off valve is configured to intermittently control a flow of the target nucleic acid solution in the second flow channel unit connecting the outlet of the reaction unit and the second inlet of the lateral flow analysis unit.

7. The real-time PCR analysis plate device of claim 1, wherein the closed line is formed by the elastic sealing film fused to the base substrate to be projected to a height of 2 mm or less on the base substrate.

8. The real-time PCR analysis plate device of claim 1, wherein:

the first shut-off valve is formed by the elastic sealing film fused into a shape of a closed line including an inlet of the first shut-off valve and an outlet of the first shut-off valve and the first shut-off valve is configured to open such that the elastic sealing film stretches due to pressure of the target nucleic acid solution entering through the inlet of the first shut-off valve and the solution exiting through the outlet of the first shut-off valve; and when an upper portion of the elastic sealing film is configured to be pressed with a valve compression unit to cause the elastic sealing film to come into close contact with the base substrate such that the inlet of the first shut-off value and the outlet of the first shut-off valve are closed as the target nucleic acid solution in an inner space of the first shut-off valve is drained.

9. The real-time PCR analysis plate device of claim 1, wherein the closed line is formed by the elastic sealing film fused to the base substrate has a width of 0.5 mm to 2 mm.

10. The real-time PCR analysis plate device of claim 6, wherein the lateral flow analysis module has a structure of lateral flow paper with a fixed nucleic acid probe, includes a loading pad attached to a front end and an absorption pad attached to a rear end, and includes one or more nucleic acid probes fixed to a plurality of linear arrays arranged perpendicularly to a flow of the target nucleic acid solution.

11. The real-time PCR analysis plate device of claim 1, wherein:

one or more pairs of dried primers or a dried primer/probe are configured to be applied to a portion adjacent to the first inlet of the reaction unit;

when the target nucleic acid solution containing polymerases is c injected, as air inside the first flow channel unit and the reaction unit is compressed, the target nucleic acid solution is mixed with the dried primers or a dried primer/probe, and the elastic sealing film is configured to be stretched and form the upwardly convex portion; and when an operation of pressing the upwardly convex portion of the elastic sealing film with a pressing block is repeatedly performed, the injected target nucleic acid solution is configured to move into the reaction unit, and a PCR reactant solution becomes homogeneous.

12. The real-time PCR analysis plate device of claim 1, wherein:

one or more dried primers or a PCR mixture including a dried primer/probe is configured to be applied to a portion adjacent to the first inlet of the reaction unit;

when the target nucleic acid solution is injected, as air inside the first flow channel unit and the reaction unit is configured to be compressed, the target nucleic acid solution is configured to be mixed with the dried primers or a PCR mixture, and the elastic sealing film is configured to be stretched and forms the upwardly convex portion; and when an operation of pressing the upwardly convex portion of the elastic sealing film with a pressing block is repeatedly performed, the injected target nucleic acid solution is configured to move, and a PCR reactant solution becomes homogeneous.

13. The real-time PCR analysis plate device of claim 6, wherein the reaction unit includes a labeled primer configured to have the ability to complementarily bind to a 5' position of a single strand of amplified DNA and a mixture for a DNA polymerase reaction and probes having nucleic acid sequences complementary to single-helix DNA synthesized by the labeled primer, wherein said mixture and said probes are fixed in a solid state.

14. The real-time PCR analysis plate device of claim 13, wherein the labeled nested primer is labeled with a fluorescent material, a chemiluminescent material, or gold nanoparticles.

15. The real-time PCR analysis plate device of claim 1, wherein the first heating block operates at a higher temperate than the second heating block.

* * * * *